United States Patent
Labib et al.

(10) Patent No.: US 10,266,793 B2
(45) Date of Patent: Apr. 23, 2019

(54) COMPOSITIONS FOR CLEANING AND DECONTAMINATION

(71) Applicant: Novaflux, Inc., Princeton, NJ (US)

(72) Inventors: Mohamed Emam Labib, Yardley, PA (US); Stanislav S. Dukhin, Goldens Bridge, NY (US); Yacoob Tabani, Basking Ridge, NJ (US); Ching-Yue Lai, Pennington, NJ (US); James L. Manganaro, Princeton, NJ (US); Peter Materna, Metuchen, NJ (US); Jeffrey C. Robertson, Rochester, NY (US)

(73) Assignee: Novaflux, Inc., Princeton, NJ (US)

( * ) Notice: Subject to any disclaimer, the term of this patent is extended or adjusted under 35 U.S.C. 154(b) by 0 days.

(21) Appl. No.: 15/718,325

(22) Filed: Sep. 28, 2017

(65) Prior Publication Data

US 2018/0094214 A1   Apr. 5, 2018

Related U.S. Application Data

(60) Provisional application No. 62/402,394, filed on Sep. 30, 2016, provisional application No. 62/563,975, filed on Sep. 27, 2017.

(51) Int. Cl.
| | |
|---|---|
| *B08B 3/04* | (2006.01) |
| *C11D 3/22* | (2006.01) |
| *B08B 9/032* | (2006.01) |
| *C11D 11/00* | (2006.01) |
| *C11D 17/00* | (2006.01) |
| *C11D 3/48* | (2006.01) |
| *C11D 17/04* | (2006.01) |
| *A61B 1/00* | (2006.01) |
| *A61B 90/70* | (2016.01) |

(52) U.S. Cl.
CPC ............ *C11D 3/222* (2013.01); *A61B 1/00* (2013.01); *B08B 9/032* (2013.01); *C11D 3/48* (2013.01); *C11D 11/0023* (2013.01); *C11D 17/003* (2013.01); *C11D 17/0013* (2013.01); *C11D 17/04* (2013.01); *A61B 90/70* (2016.02); *A61B 2090/701* (2016.02)

(58) Field of Classification Search
None
See application file for complete search history.

(56) References Cited

U.S. PATENT DOCUMENTS

| | | | |
|---|---|---|---|
| 3,209,771 | A | 10/1965 | Gogarty et al. |
| 3,225,787 | A | 12/1965 | Gogarty et al. |
| 3,852,200 | A | 12/1974 | Meyer |

(Continued)

FOREIGN PATENT DOCUMENTS

| | | |
|---|---|---|
| WO | WO9218151 A1 | 10/1992 |
| WO | WO9534275 A1 | 12/1995 |

(Continued)

OTHER PUBLICATIONS

International Search Report and Written Opinion dated Dec. 29, 2017 for Application No. PCT/US2017/053925, 12 pages.

*Primary Examiner* — Mikhail Kornakov
*Assistant Examiner* — Ryan L. Coleman
(74) *Attorney, Agent, or Firm* — Moser Taboada

(57) ABSTRACT

Provided among other things is a cleaning composition comprising: a carrier fluid; and Minute Fibrils suspended in the carrier fluid, wherein the composition is protein cleaning effective.

38 Claims, 9 Drawing Sheets

(56) References Cited

U.S. PATENT DOCUMENTS

| | | |
|---|---|---|
| 4,003,393 A | 1/1977 | Jaggard et al. |
| 4,216,026 A | 8/1980 | Scott |
| 4,254,559 A | 3/1981 | Purinton, Jr. |
| 4,270,914 A | 6/1981 | Dahl |
| 4,304,050 A | 12/1981 | Morad et al. |
| 4,406,030 A | 9/1983 | Platts |
| 4,416,703 A | 11/1983 | Scott |
| 4,473,408 A | 9/1984 | Purinton, Jr. |
| 4,481,077 A | 11/1984 | Herrick |
| 4,525,220 A | 6/1985 | Sasa et al. |
| 4,543,131 A | 9/1985 | Purinton, Jr. |
| 4,629,575 A | 12/1986 | Weibel |
| 4,805,598 A | 2/1989 | Ueda |
| 4,860,821 A | 8/1989 | Hagewood |
| 5,075,104 A | 12/1991 | Gressel et al. |
| 5,260,021 A | 11/1993 | Zeleznick |
| 5,346,339 A | 9/1994 | Himes et al. |
| 5,443,801 A | 8/1995 | Langford et al. |
| 5,527,204 A | 6/1996 | Rhoades |
| 5,731,080 A | 3/1998 | Cousin et al. |
| 5,885,133 A | 3/1999 | Williams, Jr. |
| 5,998,349 A | 12/1999 | Guillou |
| 6,037,380 A | 3/2000 | Venables et al. |
| 6,045,623 A | 4/2000 | Cannon |
| 6,272,713 B1 | 8/2001 | Lotwin |
| 6,288,154 B1 | 9/2001 | Rhoades |
| 6,541,627 B1 | 4/2003 | Ono et al. |
| 6,683,036 B2 | 1/2004 | Foley et al. |
| 6,699,331 B1 | 3/2004 | Kritzler |
| 6,797,245 B2 | 9/2004 | Nakanishi et al. |
| 6,849,581 B1 | 2/2005 | Thompson et al. |
| 6,889,400 B2 | 5/2005 | Kawazoe et al. |
| 6,967,027 B1 | 11/2005 | Heux et al. |
| 7,037,405 B2 | 5/2006 | Nguyen et al. |
| 7,306,846 B2 | 12/2007 | Dezutter et al. |
| 7,341,623 B2 | 3/2008 | Holl et al. |
| 7,393,820 B2 | 7/2008 | Soldanski et al. |
| 7,459,028 B2 | 12/2008 | Kral et al. |
| 7,776,807 B2 | 8/2010 | Canto et al. |
| 7,824,608 B2 | 11/2010 | Kuroshima et al. |
| 7,879,289 B2 | 2/2011 | Williams |
| 7,888,308 B2 | 2/2011 | Swazey |
| 7,994,111 B2 | 8/2011 | Caggioni et al. |
| 8,097,574 B2 | 1/2012 | Heath et al. |
| 8,187,056 B2 | 5/2012 | Hashish et al. |
| 8,206,349 B2 | 6/2012 | Slenker et al. |
| 8,357,378 B2 | 1/2013 | Wallace et al. |
| 8,445,422 B2 | 5/2013 | Gonzales et al. |
| 8,466,097 B2 | 6/2013 | Allef et al. |
| 8,546,316 B2 | 10/2013 | Perez-Prat Vinuesa et al. |
| 8,546,558 B2 | 10/2013 | Ankerfors et al. |
| 8,642,529 B2 | 2/2014 | Palla-Venkata et al. |
| 8,703,691 B2 | 4/2014 | Caggioni et al. |
| 8,716,213 B2 | 5/2014 | Caggioni et al. |
| 8,741,855 B2 | 6/2014 | Quave et al. |
| 8,772,359 B2 | 7/2014 | Swazey |
| 8,785,621 B2 | 7/2014 | Flury et al. |
| 8,790,301 B2 | 7/2014 | Slenker et al. |
| 8,852,643 B2 | 10/2014 | Gonzales et al. |
| 8,920,574 B2 | 12/2014 | Bhaumik et al. |
| 8,980,011 B2 | 3/2015 | Sumnicht et al. |
| 9,045,716 B2 | 6/2015 | Swazey et al. |
| 9,149,274 B2 | 10/2015 | Spivey et al. |
| 9,163,201 B2 | 10/2015 | Gonzales et al. |
| 9,193,982 B2 | 11/2015 | Sjoede et al. |
| 9,289,449 B2 | 3/2016 | Sershen et al. |
| 9,339,172 B2 | 5/2016 | Slenker et al. |
| 9,370,478 B2 | 6/2016 | Bonner et al. |
| 9,453,156 B2 | 9/2016 | Wu |
| 9,457,453 B2 | 10/2016 | Seth et al. |
| 9,492,373 B2 | 11/2016 | Canova et al. |
| 9,534,191 B2 | 1/2017 | Fernandez-Prieto et al. |
| 9,549,890 B2 | 1/2017 | Bonner et al. |
| 9,616,002 B2 | 4/2017 | Gonzales et al. |
| 9,617,459 B2 | 4/2017 | Van Engelen et al. |
| 9,650,597 B2 | 5/2017 | Konya et al. |
| 9,677,030 B2 | 6/2017 | Napolitano |
| 9,693,675 B2 | 7/2017 | Matta et al. |
| 9,862,916 B2 | 1/2018 | Van Engelen et al. |
| 10,100,269 B2 | 10/2018 | Fernandez-Prieto et al. |
| 2003/0121532 A1* | 7/2003 | Coughlin .................. A61L 2/02 134/7 |
| 2003/0213501 A1 | 11/2003 | Thomson et al. |
| 2004/0000012 A1 | 1/2004 | Scarpello et al. |
| 2005/0220727 A1* | 10/2005 | Lupia ...................... A61K 8/41 424/59 |
| 2006/0020126 A1 | 1/2006 | Kopesky et al. |
| 2006/0249265 A1 | 11/2006 | Scarpello et al. |
| 2007/0141095 A1 | 6/2007 | Simonnet |
| 2007/0151680 A1 | 7/2007 | Scarpello et al. |
| 2007/0199668 A1 | 8/2007 | Scarpello et al. |
| 2009/0095324 A1 | 4/2009 | Crowther et al. |
| 2010/0009891 A1 | 1/2010 | Canto et al. |
| 2010/0210501 A1* | 8/2010 | Caggioni ............... C11D 3/222 510/338 |
| 2010/0221294 A1 | 9/2010 | Kurek et al. |
| 2011/0262504 A1 | 10/2011 | Deleersnyder et al. |
| 2012/0090192 A1 | 4/2012 | Oevreboe et al. |
| 2012/0100367 A1 | 4/2012 | Holtan et al. |
| 2013/0072417 A1 | 3/2013 | Perez-Prat Vinuesa et al. |
| 2013/0098407 A1 | 4/2013 | Perlman et al. |
| 2014/0128480 A1 | 5/2014 | Swazey et al. |
| 2014/0238444 A1 | 8/2014 | Arai |
| 2015/0191681 A1 | 7/2015 | Gonzales et al. |
| 2015/0210957 A1 | 7/2015 | Napolitano |
| 2015/0210967 A1 | 7/2015 | VanEngelen et al. |
| 2015/0305819 A1 | 10/2015 | Krause |
| 2016/0222275 A1 | 8/2016 | Galindo et al. |
| 2016/0331703 A1* | 11/2016 | Myntti ................. A61K 9/0014 |
| 2017/0044468 A1* | 2/2017 | Gori ................... C11D 3/38636 |
| 2017/0121908 A1 | 5/2017 | Holtan et al. |
| 2017/0191003 A1 | 7/2017 | Fernandez-Prieto et al. |

FOREIGN PATENT DOCUMENTS

| | | |
|---|---|---|
| WO | WO03040284 A1 | 5/2003 |
| WO | WO2008109270 A1 | 9/2008 |
| WO | WO2010070354 A1 | 6/2010 |
| WO | WO2012040314 A1 | 3/2012 |
| WO | WO-2012052306 A1 | 4/2012 |
| WO | WO2012065924 A1 | 5/2012 |
| WO | WO2016100822 A1 | 6/2013 |
| WO | WO-2014082951 A2 | 6/2014 |
| WO | WO2014154348 A1 | 10/2014 |
| WO | WO2015180844 A1 | 12/2015 |
| WO | WO2016086951 A1 | 6/2016 |
| WO | WO2016166179 A1 | 10/2016 |

* cited by examiner

COMPOSITIONS FOR CLEANING AND DECONTAMINATION

This patent application claims the benefit of Provisional Patent Application U.S. Ser. No. 62/402,394, filed Sep. 30, 2016, including its appendix, and Provisional Patent Application U.S. Ser. No. 62/563,975, filed Sep. 27, 2017 (NOVA003P2), including its appendices, all of which are incorporated herein by reference in its entirety.

Embodiments of the invention pertain to compositions, methods and apparatus for the decontamination, cleaning, sanitization, disinfection, sterilization, storing in disinfected or sterilized condition, and treatment, of long narrow lumens, channels and tubes such as in endoscopes, other luminal medical devices as well as other surfaces irrespective of geometries or material of construction.

Though the invention is applicable to many fields, the field that primarily engendered the current invention is the field of cleaning and sterilizing endoscopes, and the long narrow channels found in these devices. Infections traced to endoscopes have been a tremendous problem, yet the mechanical complexity of the devices means that it has been impractical to utilize single use devices, and even the components cannot at this time be switched out with single use components. The construction and heat-sensitive materials of flexible endoscopes generally preclude the use of high temperature steam for sterilization, and the long length and the small cross-sectional size of the various internal tubing channels cause fundamental difficulty in cleaning, disinfecting, and sterilizing these channels. While there are many examples of serious infection reported, a particularly serious report was of two patient deaths at the UCLA Medical Center in 2015 from carbapenem-resistant Enterobacteriaceae (CRE) infection transmitted by contaminated duodenoscopes, namely Endoscopic Retrograde Cholangiopancreatography (ERCP) Duodenoscopes. CRE contamination has been linked to biofilm growth in ERCP endoscopes, and this biofilm can be related to inability to clean the internal channels of the endoscope or other parts of the elevator section of the endoscope.

Biofilms are highly resistant to standard cleaning, and a common cause of infectious diseases, especially from medical devices. Biofilms adhere on surfaces utilizing layers of extracellular polysaccharide substances (EPS) in which the microorganisms are embedded. EPS provide biofilm structural stability and also protection from environmental factors such as antimicrobial substances. Though organisms may be dormant in a biofilm, the biofilm will release bacteria in the more infectious planktonic form.

The suction and biopsy channel ("SB channel") most consistently contacts with materials that create a risk of infection, and the growth of biofilm. It also typically has an inner diameter (e.g., >2.8 mm such as 3.2 mm or 3.7 mm) that allows for more vigorous cleaning, including scrubbing with a brush. Yet, Applicant has found that standard protocols do not remove biofilm, and especially does not remove build-up biofilm (BBF, described further below). FIGS. 1A and 1B show scanning electron microscope images (SEMs) of an SB channel lumen after manual brushing five times according to a standard protocol. The SEMs show build up biofilm strips that are not removed by manual brushing. Despite extended brushing, biofilm removal from the channel lumen is incomplete. FIG. 1B is at higher magnification, such that the outlines of the bacteria can be seen.

Further a typical endoscope has additional, narrower channels, such as air, water, irrigation, forced jet and elevator channels. These channels can have for example an ID of 1.5 mm or less. These channels are not immune to acquiring biological contamination, including contamination migrating from other parts of the endoscope. These channels cannot be conventionally brushed. Given the strong limitations on tools for cleaning these channels, they represent a major source of concern for spreading infection.

Beyond the narrow width of SB and narrower channels, another challenge is that the material used, most frequently Teflon®, is resistant to wetting with aqueous fluids, making it more likely that patches of material are not effectively contacted with cleaning fluids (such as rinse agents, cleaners, disinfectants, sterilants, enzyme solutions, and the like). This lack of wetting can also affect high-level disinfectants such as glutaraldehyde, hydrogen peroxide, ortho-phthalaldehyde, peracetic acid, and the like. The narrow width of these channels, and the pressure limits on their operation, mean that the hydrodynamic detachment force (HDF) that can be generated by conventional flow is limited.

After traditional cleaning and disinfecting, the endoscope is typically flushed with alcohol, and purged with air to dry the interior channels. However, publications by Cori L. Ofstead and co-authors have shown that pockets of moisture remain, which promotes biofilm formation.

One aspect of the current invention was the realization that gels or other high viscosity fluids pumped through these channels at pressures falling within the operating parameters for an endoscope (e.g., 28 psi) can provide shear stress on the surfaces of the channels higher than that of conventional water-based cleaners to more effectively remove contaminants. Applicant has shown this base invention to be effective in improving the removal of bacteria and organic soil (protein, lipids, carbohydrate, hemoglobin or similar substances) from the channels. Without more, it is less effective in removing BBF.

What Applicant discovered was very effective in removing biofilm and even BBF were compositions (not necessarily gels) containing fibrillated polymers. These are polymers with thicker (often crystalline or semi-creystalline) polymer bundle segments, from which branch thinner polymer bundle segments. With cellulosic fibrillated polymers, there may be three tiers of polymer bundles, as well as polymer single chains. Without being bound by theory, it is believed that as this type of polymer moves across the surface to be cleaned in a network, the stiffer components are periodically shifted to collide and interact with the surface, or to cause segments of branched polymer bundles to so collide, providing localized shear stress that provides contaminant-dislodging force. The localized shear stress periodically applied is believed to be far higher than the bulk shear stress. The network of fibrillated material provides thousands of such contacts to any narrow area, and also provides a network for entrapping and carrying the contaminants out of the channels.

SUMMARY

Embodiments of the disclosure comprise a cleaning and storage compositions, methods of use, devices utilizing, and the like, substantially as shown in and/or described in connection with at least one of the figures, as set forth more completely in the claims. Various advantages, aspects and novel features according to embodiments of the disclosure, as well as details of an illustrated embodiment(s) thereof, will be more fully understood from the following description and drawings.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1A:
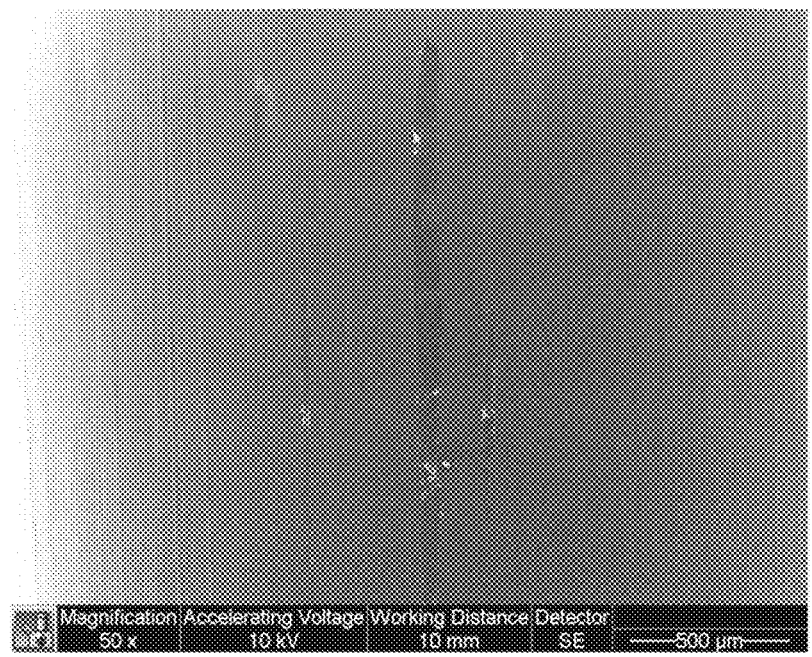
FIGS. 1A (see 500 micron bar) and 1B (see 10 micron bar) depict a biofilm remaining after traditional cleaning.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Minute Fibrils—General

Figure 2:
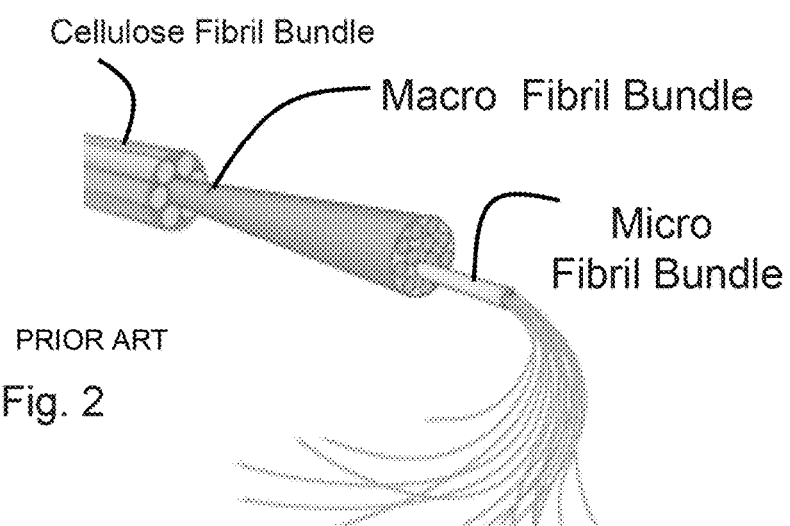
FIG. 2 shows a schematic of the structure of cellulose fibril bundles.

"Minute Fibrils" (MFs) is a term coined to encompass what the industry terms as microfibrillated cellulose and nanofibrillated cellulose (which are basically the same thing) and substantially equivalent structures made from synthetic polymers, including without limitation those made by the Lyocell melt spinning process or similar processes. The structure of cellulose is illustrated in FIG. 2 (adapted from nutrition.jbpub.com/resources/chemistryreview9.cfm). The structure of microfibrillated cellulose can be discussed with reference to this figure. In native cellulose structures there are native cellulose fibers (diameter=about 20,000 nm to about 60,000 nm), smaller macro fibril bundles and still smaller micro fibril bundles. There are believed also to be single polymer chains (which do not visualize as easily in microscopy). Microfibrillated cellulose is cellulose that has typically been treated mechanically, chemically, enzymatically, or with combination treatments to separate out macro fibril bundles and micro fibril bundles. These can loop off larger fibril bundles, or extend from larger fibril bundles. It may be that there are unconnected micro fibril bundles, but the amounts are believed to be small, and the fibril bundles are believed to associate with the connected fibril bundles. There can be two or more tiers of diameter sizes. What is important is that the micro fibril bundles (or their analog) are connected to stiffer, larger bundles.

A useful measurement parameter for Minute Fibrils is the hydrodynamic size (HDS), especially the mean HDS (MHDS). This is measured by laser diffraction of a highly dilute suspension, using a Mastersizer 3000 (Malvern Instruments), [José et al., On the morphology of cellulose nanofibrils obtained by TEMPO-mediated oxidation and mechanical treatment, Micron, 72, 28-33 (2015)]. Though energy is applied (by sonication) to separate structures, it is not clear whether the entity measured is a single structure, or a floc of two or more. The substance so measured is a "fibrillated entity."

It has been found that microfibrillated cellulose that has been processed to the extent that the MHDS is as low as about 20 micron (micrometer) is less effective, if provided on its own, than microfibrillated cellulose with MHDS of for example 30 to 70 micron. Surprisingly the larger microfibrillated cellulose is in some embodiments even more effective if appropriately mixed with smaller microfibrillated cellulose. These and all other lessons drawn from cellulose are expected to be applicable to synthetic Minute Fibrils as well. Thus, in embodiments, it is useful to mix a Minute Fibril composition having one MHDS with one having a MHDS of 50% or less. In embodiments, a ratio having more of the larger Minute Fibril component (by dry weight) is used, such as a ratio of about 1.5:1 or more, such as about 2:1 or more, or about 3:1. In embodiments, the distribution of the source compositions is tight enough such that the mixture is indicated in the product by a bimodal (or for further mixtures, multi-modal) distribution.

In embodiments, the Minute Fibrils comprise relatively large diameter fibrils, which can be expected to provide stiffness, which can be termed "Type B" Fibrils, for example having diameter from about 100 nm to about 20,000 nm (20 micron). They can further comprise "Type A" fibrils of a small diameter range, e.g., 10 to 90 nm. SEM images show Type A fibrils connected to Type B fibrils. This is not to say that all Type A fibrils extend from Type B fibrils.

Type A fibrils are also referred to herein a "nanofibrils." These are believed to be more involved in entangling fibrillated entities.

For cleaning narrow channels (e.g. SB channels or narrower), the length of the starting fiber bundle can be important. Length can be difficult to measure after the fiber bundle has been processed to Minute Fibrils. Favorably the number average length is about 1000 microns or less, or about 800 microns or less, or about 500 microns or less. "Narrow channels" are channels or tubes with ID of about [6 mm] or less, and sufficient length that cleaning with brush is not practical or tends to be ineffective against BBF, such as outlined herein for SB channels.

For cleaning, typically, a "fibrillated network" is used. A fibrillated network is a 3-D network structure made from the interaction of fibrillated entities as the result of entanglements of fibrils as well as due to hydrogen bonding (or other non-covalent bonding mechanisms including electrostatic) when the fibrillated materials are properly mixed with water or solvents.

Without being bound by theory, it is believed that when a suspension, dispersion, network or mixture of Minute Fibrils flows in channel or the like, the fibers, fibrils or their flocs (aggregates that move and tumble as a unit) or their nanostructures as described herein contact or nearly contact the surface of the channel or tube during flow, resulting in scraping, abrading, removing, detaching, desorbing or effecting localized brushing-like action at a very small size scale. These cleaning processes occur when the gel-like network structure such as Minute Fibrils moves past the wall while the gel structure such as Minute Fibrils are in contact or nearly in contact with the wall. This action is believed to repeatedly create localized high hydrodynamic detachment force or even make direct contact with the surface being cleaned, with that force or stress being sufficient to detach, desorb and remove contaminants.

The very large specific surface area of the Minute Fibrils can significantly facilitate material transfer and removal of contaminants from the walls of channels, tubes or confined space during flow. The specific surface area of for example some nano- or microfibrillated cellulose material can be more than about 10 m^2/g and up to more than 300 m^2/g and in some cases can be more than one or two billion m^2/g, which can produce effective and efficient treatment and can clean walls as they contact or nearly contact them during flow. The large surface area can facilitate adsorption of contaminants and can trap contaminant fragments during cleaning. The surface area can be estimated from SEM micrographs, adsorption of nitrogen or other gas, surfactant or other molecular probe with known surface area or combination of methods as it is known in the colloid and surface science or materials science literature.

For the purposes of the claims, measurement is by the adsorption of nitrogen onto the surface of the material. This technique is based on the Brunauer-Emmett-Teller (BET) theory of the adsorption of gas molecules on a solid surface. In this technique, the material is prepared by first desorbing whatever is adsorbed onto the surface of the material, and then the material is placed in an environment where it can adsorb nitrogen. The amount of gas adsorbed at a given pressure indicates the specific surface area of the material. This measurement of the amount of the amount of adsorbed gas can be made by measuring the change in the amount of gas present, or by measuring the change in the weight of the material.

In certain embodiments, the specific surface area for the Minute Fibril composition providing the major portion (50% or more) of Minute Fibrils is about 30 m^2/g to about 300 m^2/g, or higher in some cases.

A composition has a protein cleaning effective amount of fibrils plus any gel-forming polymer or any stiffening components if that amount, formulated at one or more of pH 7 or 9 in CS-19 (described below) would clean Austrian Soil-derived protein (applied as described below) from the inner surface of six foot length of 3.2 mm ID PTFE tubing to reduce adherent protein by 50-fold or more to a level of about 6.4 µg/cm2 or less.

A BBF cleaning effective amount of fibrils plus any gel-forming polymer or any stiffening components is one that if that amount, formulated at one or more of pH 7 or 9 in CS-19, would remove BBF (formed as described below) from the inner surface of six foot length of 3.2 mm ID PTFE tubing as measured by SEM analysis.

A composition (for any gel, fiber or other cleaning embodiment) is protein cleaning effective if it cleans Austrian Soil-derived protein (applied as described below) from the inner surface of six foot length of 3.2 mm ID PTFE tubing to reduce adherent protein by 50-fold or more to a level of about 6.4 µg/cm2 or less.

A composition (for any gel, fiber or other cleaning embodiment) is BBF cleaning effective if it removes 90% or more of BBF from the inner surface of six foot length of 3.2 mm ID PTFE tubing as measured by SEM analysis.

For formulations configured for open surfaces and having too much viscosity for measuring protein or BBF removal in a tube, if formulations included within the components are protein cleaning or BFF cleaning, the formulation is so effective.

Useful concentrations of Minute Fibrils can include for example from about 0.2% w/w to about 4% w/w. The amount can vary with the specific characteristics of the Minute Fibrils and the carrier fluid. For example, with one Exilva (described below) Minute Fibril composition, 1.2% by weight was not sufficient to erode and remove BBF in 20 minutes, while compositions containing 1.4% or 1.7% or 1.9% could erode and remove BBF in about 5 to 10 minutes.

In certain embodiments, flocs of the Minute Fibrils have a mean diameter of about 50 to about 100 microns Cellulosic Minute Fibrils—Production Methods of production of Minute Fibrils include mechanical processing, TEMPO-catalyzed processing, and enzymatic processes, and combinations of thereof. Exilva grade microfibrillated cellulose (made by Borregaard) is made by a purely mechanical process with many passes through Borregaard's processor machine, which includes a form of microfluidizer. The Lyocell process, which can be used with cellulose, is similar to what is used in making Nylon and it can also be used with acrylics or other polymers. TEMPO (a common name for a catalyst whose chemical name is (2,2,6,6-Tetramethylpiperidin-1-yl)oxyl or (2,2,6,6-tetramethylpiperidin-1-yl)oxidanyl) is used in some processes to induce partial cleavage in the cellulose. Sodium hypochlorite or sodium bromide can also be used as oxidizing agents (for example along with TEMPO) for cleavage, in combination with mechanical force. A variety of mechanical processes can be used such as high pressure homogenization, microfluidization, grinding, refinery-based processes, cryocrushing, and high intensity ultrasonication. It can include directing jets of fiber-containing liquid to impinge on one another. A process may use for example, two passes through a grinder or refiner, and multiple passes through a homogenizer.

Materials made by Borregaard have subclassifications including:

TABLE 1

| Sub-Grade | Mean Hydrodynamic size | Size Range |
|---|---|---|
| Exilva Forte | ~20 micron | ~1 to ~1000 micron |
| Exilva Piano (various grades) | ~36 to ~60 micron | ~1 to ~1000 micron |
| Exilva Piano Light | ~70 micron | ~1 to ~1000 micron |
| Sensifi (in admixture with CMC) | ~100 micron | ~1 to ~1000 micron |

As analyzed by numerous SEMs at several magnifications, some illustrative cellulosic Minute Fibrils have the following features:

TABLE 2

| Microfibrillated Cellulose | Fibers (Type B) | | Fibrils (Type A) | |
|---|---|---|---|---|
| | Diameter | Length | Diameter | Length |
| Exilva Forte | 0.5-3 µm | 10-100 µm | 30-60 nm | >2 µm |
| Exilva Piano | 0.1-20 µm | 5-150 µm | 50-70 nm | 2-3 µm |

TABLE 2-continued

| Microfibrillated Cellulose | Fibers (Type B) | | Fibrils (Type A) | |
| --- | --- | --- | --- | --- |
| | Diameter | Length | Diameter | Length |
| Exilva Piano Light | 0.3-20 μm | 20-200 μm | 20-75 nm | 1-5 μm |
| Sensefi | 0.25-15 μm | 5-60 μm | 30-60 nm | 0.4-1.0 μm |

The results of Table 2 include a summary of the SEM analysis of some of the fibrillated materials as described in embodiments of the invention. The top three materials listed in the Table represent different degrees of fibrillation and are sold without other additives. The fourth material (Sensefi) is made by a special process and as sold includes carboxymethyl cellulose (CMC). The fibrillated material, made as dilute suspension, was deposited to SEM stubs and coated according to accepted SEM imaging methods. The data is divided based on manual image analysis where fibers and fibrils are listed separately. Diameter and length of fibers and fibrils are includes as seen in the micrographs. The ranges of diameter and length of fibers and fibrils include the most prevalent sizes. At least 1000 fibers and 1000 fibrils were examined for each of the four materials. Diameters can be highly accurate since they can be obtained from the micrographs. On the other hand, the lengths can be less precise since it difficult to ascertain because of high magnification of the SEM images. The SEMs for each material was obtained at 100×, 1,000×, 2,000×, 10,000×, 50,000× and 10,0000×. In an embodiment of the invention, the diameter and length of the fibers and fibrils represent the ranges used to prepare the networks described in the specification. This can be important since the diameter and length are believed to contribute to the mechanical properties of the network, especially strength, stiffens and rigidity which are important for cleaning according to the invention. Although SEMs provide specific data about the morphology of the fibrillated materials, other definitions of the fibrillated materials can be obtained from laser scattering results of the equivalent hydrodynamic volume as described elsewhere herein. Additional description of the fibrillated materials include viscosity data and rheological date when suspended in liquid as described elsewhere herein.

Microfibrillated fibrous materials are now commercially available from such suppliers as: Borregaard (Sarpsborg, Norway) (products include Exilva, Sensefi); Wiedmann Fiber Technology (Rapperswil S G, Switzerland) (WMFC_QAdvanced); Engineered Fibers Technology LLC (Shelton, Conn.) (EFTec™ nanofibrillated fibers); American Process, Inc. (Atlanta, Ga.) (BioPlus® Fibrils); Celluforce (Montreal, Canada); Forest Products Laboratory (US Department of Agriculture); Lenzig AG (Austria)(products include Lyocell); Weyerhaeuser (Seattle, Wash.)(products include Lyocell); and other suppliers in Scandinavia and Japan.

Synthetic Minute Fibrils—Production

Synthetic polymers can be formed into macro fibril structures for example by spinning (extruding) a solubilized formulation. For example, cellulosic polymers can be so extruded, for example using N-methyl-morpholin-N-oxide (NMMO) as the solubilizing solvent. Other solvents can be chosen as appropriate for solubilizing the polymer in question, such as acrylics and others. The spun fiber can then be cut and mechanically converted into a Minute Fibril form as outlined above. For example, Engineered Fibers Technology (Shelton, Conn.) sells fibrillated polymers of Acrylic (CFF®, acrylic copolymer), Lyocell (Tencel®, for wood pulp), LCP (Vectran®, aromatic polyester), PBO (Zylon®, crystalline polyoxazole), Para-aramid and Cellulose (wood and non-wood).

Gels for Cleaning

A gel is a deformable material or a fluid-like composition. For use in cleaning long narrow channels a gel should have a yield shear stress above which it starts to flow. A gel typically comprises a network of entangled macromolecules, fibers or fibrils, or crowded swollen microgel particles. For applied shear that is less than the yield shear stress, the gel does not flow at all or the gel can move as a single body or intact network as long as the network is not destroyed during act of movement. For applied shear stress that is above the yield shear stress, the gel flows as the network is destroyed or partially destroyed. The yield shear stress behavior can be a result of a network structure within the gel, which to some degree breaks apart when yielding occurs. A gel can also be non-Newtonian, such as shear-thinning, as a description of its rheological flow properties for flow that occurs beyond the yield point at which the gel begins to flow. A composition of Minute Fibrils can have these properties.

Gels can be made from hydropolymers polymers such as Carbopols (high molecular weight, polyacrylic acid polymers). Carbopols or carbomers are sold commercially under the name Carbopol®, by the Lubrizol Corporation, Wickliffe, Ohio. These polymers may be cross-linked and insoluble in water although they do not have to be cross-linked. A network structure of these gels can be seen in cryo-sections visualized by a Scanning Electron Microscope. This is further described in: Rheological properties and microstructures of Carbopol gel network system, by Jong-Yun Kim et al., Colloid and Polymer Science, July 2003, Volume 281, Issue 7, pp 614-623. Even at about 0.1 or 0.2% concentration by weight in water, a fibrous three-dimensional gel network system forms. As visualized, the network can show fractal aggregates. In embodiments, the gel utilized shows such fractal aggregates. As the amount of polymer increases, the strings or structures or swollen particles of the fibrous network become thicker and form honeycomb-like structures which can possess a yield shear stress.

As explained in a data sheet for Carbopol® polymer, the polymer can be either soluble or insoluble in water. If the polymer is linear rather than crosslinked, the primary particle would be a collection of linear polymer chains, intertwined but not chemically bonded via covalent bonding. A linear polymer form of Carbopol® is commercially available as Carbopol 907 and it is soluble in water. In contrast, crosslinked polymers generally do not dissolve in water, and can be termed "water-insoluble." All Carbopol® polymers other than Carbopol 907 are crosslinked, and are water-insoluble. Polyacrylic acid polymers branded Pemulen®, and Noveon® are also insoluble. These polymers swell in water up to 1000 times their original volume (representing ten times their original diameter) to form a gel when they are exposed to a pH environment above 4-6. The form of Carbopol® polymer exemplified herein has a Molecular Weight of $3\text{-}6\times10^{\wedge}6$ Daltons, with the primary particles having a dimension of 20-70 nm in diameter. The primary particles in turn are believed to form secondary aggregates having a typical size of the order of 0.2 μm. The secondary aggregates in turn are believed form tertiary aggregates having a typical size range of the order of 0.2-2 μm. A process for forming the composition of Carbopol used herein can start with wetting Carbopol in water to form a dispersion. This can be done with water, and the resulting suspensions can for example have a pH in the range of approximately 3 to 4, and in this situation the dispersion has a relatively low viscosity, which can be close to the viscosity of water. After this dispersion is subjected to neutralization with Triethanolamine or an alkali such as sodium hydroxide or potassium hydroxide, which raises the pH ~8, the particles swell to approximately 1000 times their original volume, which produces a fluid that has high viscosity and high yield shear stress. The resulting viscosity can be 2,000 to 10,000 cP (centipoise) at Carbopol® concentrations of 0.2% to 0.3%, for the shear rates typically used herein. Thus, the structure and properties of Carbopol in water are significantly responsive to chemical properties of the carrier fluid, such as the pH of the carrier fluid.

Such carbopol gels have been shown to have a yield shear stress that makes it feasible to pump them through the channels of an endoscope. Their shear thinning properties assist in such pumping through channels.

Carbopol is not the only substance that forms gel structures in water. Examples of other substances that exhibit such behavior include polyacryamides, other synthetic polymers, cellulosics, and many natural polymers of plant, animal, or sea origins including weeds and algae. Some of useful gels can exhibit yield shear stress and others may not have yield shear stress but still can be effective in cleaning a good range of contaminants weaker than BBF Useful concentrations of gel-forming polymer can be for example from about 0.05% w/w to about 2% or 3% w/w.

A gel of this type can be used in combination with Minute Fibrils.

Gel-Minute Fibril Combinations

Given combinations where the concentration of the non-MF gel-forming substance does not by itself produce a gel, and the concentration of the Minute Fibrils does not by itself produce a gel; it has been found that the combination of the concentration of the together can produce a gel or network. Other such combinations can also be useful. It has been found that such combination formulations produce a cleaning effects when for example flows through a tube or passageway. It is believed, although it is not wished to be limited to this explanation, that a formulation comprising a non-MF gel-forming substance and Minute Fibrils can have less of a tendency to clog a passageway or to leave Minute Fibrils behind in the passageway, as compared to a gel of similar properties or similar cleaning effectiveness that is formed by the presence of Minute Fibrils without the additional presence of a non-MF gel-forming substance. This is advantageous because a clog, especially a clog that results from fibers alone, could require additional steps to unclog, or it might even be impossible to unclog. A clog could require expensive repairs to an endoscope or could even be impossible to repair. Water or liquid vehicle including cleaning ingredients can be used to form the composite gel according to embodiments of the invention.

In an embodiment, the yield shear stress of a Minute Fibril network can be increased by incorporating a gel-forming substance like Carbopol that possesses high yield shear stress by itself. It is known that some cross-linked carbopol gels can have high yield shear stress more than 100 Pa when made at pH about 7.0 to 9.0. On the other hand, some Minute Fibril networks can have low yield shear stress values, for example between 1 to 60 or 100 Pa. Accordingly, a composition comprising a ratio of Minute Fibrils and carbopol (or other yield shear stress forming substance) can produce a stronger network with high composite yield shear stress. This composite network can possess higher strength than a network made with Minute Fibrils only. As described elsewhere herein a network composition with higher strength can be advantageous with respect to cleaning tenacious contaminants such as build up biofilm. The proportion of Minute Fibrils and the yield shear stress contributing substance can be adjusted so that effective cleaning can be obtained.

In an embodiment, inclusion of a small concentration of an ionic polymer such as carboxymethyl cellulose (as exemplified by one having molecular weight more than 250,000 and 80% substitution at about 100 to 200 ppm by weight) in the Minute Fibril composition can aid in cleaning BBF. Without being bound by theory, the small concentration of such charge-providing material is believed to disperse the fibrils due to electrostatic repulsion and make them extend so that they can participate in producing more entanglement, which leads to making a stronger network. This discovery can be extended to using cationic polymers if positive electrostatic charge is desired. The amount of polymer is judiciously added to avoid creating weaker networks or lubrication of the network-surface boundary.

Analytical BBF

A standard protocol has been used to produce a BBF for testing the compositions of the invention. This protocol, described in detail in Example 2, involves one week of growth including applications of glutaraldehyde at defined times during that week as documented by Alfa et al. [Reference: A novel PTFE-channel model, which simulates low levels of culturable bacteria in build-up biofilm after repeated endoscope reprocessing. Alfa et al., Gastrointestinal Endoscopy 85(5), Supplement, pp. AB67-AB68, 2017].

Stiffening or Abrasive Components

Additional components can be added to provide a stiff network, which can be useful to supplement the effects of the stiff components of Minute Fibrils, or provide abrasives to Minute Fibrils or gels. Non-polymer abrasives can also be added. The manner in which these components are added can have a notable effect. Without being bound by theory, if introduced with high energy, they are anticipated to uniformly distribute. If added with less energy, e.g., whisking, they are anticipated to more strongly populate the outer parts of flocs of Minute Fibrils. In certain embodiments, such as for example cleaning optical lenses, extra care may be taken with the selection these components to avoid damage. In certain embodiments, such as cleaning or sharpening blades, the selection of these components may be made to accentuate microabrasion.

Stiffening Polymers

Stiffening polymers are exemplified by microcrystalline cellulose (MCC), though other polymers that can provide this function can be substituted. MCC is available in various grades from several sources and vendors, and can be obtained from FMC Corporation, Newark, DE, under the name Avicel®. Microcrystalline Cellulose is made by a hydrolysis process which removes the amorphous fraction from cellulose fibers and controls the degree of polymerization at the same time. In embodiments, MCC fibers are not as elongated (as described by length/diameter ratio) as some of the Minute Fibrils described herein. Microcrystalline Cellulose is safe and is used extensively to make tablets and other pharmaceutical and food products.

Microcrystalline Cellulose can form gels that have increased viscosity when standing, especially when the Microcrystalline Cellulose is co-processed with carboxymethyl cellulose (CMC) polymer. Because of its elongated shape and stiff crystalline nature, Microcrystalline Cellulose does not readily form gels that have entangled network structures; however, it can make some kind of 3D network that forms weak gels over one or more weeks. Accordingly, gels based on MCC-CMC may be weaker (in terms of yield shear stress) compared to gels made from Minute Fibrils.

Because of its crystalline nature, MCC can provide rigidity, stiffness and hardness to the Minute fibril compositions described herein. In addition, when MCC is included as a component of the Minute Fibril network at sufficient concentration, from about 0.1 to 10% by weight and preferably at about 1 to 3% by weight of the Minute Fibril composition, it can provide a stronger network (or increase yield shear stress and storage modulus) and abrading action at the wall or surface to remove strong contaminants such as for example build up biofilm.

If added with high energy, the effect of MCC on improving BBF cleaning is less than if added to a Minute Fibril network with lower energy.

Solid Particles

In yet another embodiment of the invention, the composition may comprise Minute Fibrils (or gel) and also solid particles. In embodiments, the hardness of fluid Minute Fibril network compositions can be increased by including solid particles at suitable concentration from 0.1 to 5% and preferably from 0.2 to 3% by weight of the Minute Fibril composition. Accordingly, Minute Fibril compositions including solid particles or fibers are effective in removing biofilms and contaminants from passageways and surfaces.

Hardness can be described, at least qualitatively, using the Mohs hardness scale that was originally developed in the field of mineralogy, or another scale. It is believed that the hardness of cellulose is about 3 on the Mohs hardness scale. As an example, the particles may be simple inorganic substances, which may be insoluble or poorly-soluble in water. For example, Calcium Carbonate (CaCO3) is one such substance. Calcium carbonate is believed to have a Mohs hardness of around 4. Colloidal silica (silica gel) is another possible substance. Colloidal silica is not as hard as ordinary silica or quartz. The Mohs hardness of silica gel is around 4, similar to that of CaCO3. Silica gel is amorphous and is not very scratchy. Ordinary silica or quartz, in contrast to colloidal silica, is hard enough to remove biofilm, but also is hard enough to scratch typical polymeric materials used for the wall of the passageway. Quartz, which is ordinary silica, like sand, has a Mohs hardness of 7. Silica gel is FDA approved for use as a dentifrice also is approved for exfoliating, and it does not cause silicosis.

Another suitable particle material of the inventive composition could include crushed olive pits and crushed cashew nut, both of which are available commercially in a range of particle size from 50 microns to more than 500 microns. Such material can be mixed in with other components of the Minute Fibril composition. Particles or fibers used can include: Wool made by Goonvean, Nylon made by Goonvean, Olive Stone made by Goonvean, Syloid EXF150 (SiO2) made by W. R. Grace, FMC Lattice NTC-80 Microcrystalline Cellulose, FMC Lattice NTC-61 Microcrystalline Cellulose, FMC NT-100, FMC NT-200, Precipitated CaCO3, and the like.

Insoluble or poorly-soluble material can also be formed within the composition by a precipitation reaction that could take place upon the mixing of appropriate aqueous-solution ingredients. Examples include but are not limited to precipitated calcium carbonate, silica, calcium phosphates including hydroxyapatite, fluorophosphates, alumina and other materials. The particles formed within the network can be crystalline, amorphous or comprising mixed phases as desired. The particle size and size distribution of particles formed within the network can for example range from 50 nanometers to several microns possibly in the range from 0.5 to 100 microns, or even up to 500 microns or more. For example, a reaction that produces insoluble calcium carbonate particles within the network includes mixing calcium chloride and sodium carbonate which can be formed in situ within the Minute Fibril network during preparation. Other reactions include: reaction between various carbonates (e.g. sodium carbonate) and calcium hydroxide; reaction of soluble calcium salt and carbon dioxide gas; reaction between ammonium carbonate and calcium hydroxide or other reactions known to form calcium carbonate as is known in inorganic chemistry. The sizes of such produced precipitate particles can be dependent upon the rate and other conditions at which the reaction takes place. Scanning Electron Microscope examination has shown that precipitated calcium carbonate is distributed onto the fibers and fibers and on the spaces between them within a Minute Fibril network. Precipitated particles that adhere to fibril surfaces are especially useful as they can modify the stiffness and hardness of the network and can thus improve the abrasion properties of the network. Composition comprising in situ precipitated particle were found to be effective in removing strong build up biofilms.

Further examples of solid particles are provided in Table 3.

TABLE 3

| Product | Source |
| --- | --- |
| Wool CMW80; Dia.: 20-30 μm (>90%); Length: Max: 200 μm (>95%) | Goonvean Fibres (goonveanfibres.com) |
| Nylon (Polyamide) Fibre WN60; Dia.: 10-20 μm ± 10% (>95%); Length: Max: 250 μm (>90%)(Average (>50%): ~125-250 μm | Goonvean Fibres |
| Viscose Fibre RM60; Dia.: 8-25 μm ± 10% (>95%); Length: Max: 250 μm (>95%)(Average (>50%): ~100-225 μm | Goonvean Fibres |
| Olive Stone Grit EFOG; Max: 355 μm (>99%); Passing: 200 μm (<15%); Passing: 150 μm (<4%) | Goonvean Fibres |
| Silica Syloid EXF 150 (150 μm) | W. R. Grace Co., Columbia, MD |
| Silica Syloid EXF 350 (350 μm) | W. R. Grace Co. |
| Silica Syloid EXF 500 (500 μm) | W. R. Grace Co. |
| Hydrocarb 60-FL 78% 3996200 | Omya Inc., Cincinnati, OH |
| Hydrocarb PG3-FL 73% | Omya Inc |
| Omya Syncarb S160-HV 20% 4430400 | Omya Inc |
| Omya Syncarb S240-HV 20% | Omya Inc |
| Silica Gel, 200-425 mesh | Sigma-Aldrich, Inc., St. Louis, MO |
| Silica Gel, 28-200 mesh | Sigma-Aldrich, Inc. |
| Calcium Carbonate | Sigma-Aldrich, Inc. |

Carrier Fluid Components

The gel or Minute Fibrils (or both) are suspended in a carrier fluid, such as without limitation an aqueous fluid. Typically, there will be a surfactant component configured to help loosen the attachment of a contaminant to a surface.

Surfactants or Dispersants

In embodiments of the invention, the fluid composition can comprise a surfactant or a surfactant package or mixture containing one or more surfactants. During for example preliminary cleanup of a medical device (the bedside prep phase), surfactants can prevent and decrease strong adhesion of patient's biological material such as fecal matter, blood, mucus, protein and organisms that has recently contacted the surface of an endoscope or device, and also can help to prevent drying of such material onto surfaces. Surfactants can also promote wetting of hydrophobic surfaces and prevent de-wetting of surfaces by promoting formation of a thin film on the surface if drainage of composition would take place. Surfactants also can help in the removal of such materials (organic soils, biofilms, organism and patient materials such as fecal matter) from the surfaces and can lower the adhesion force of contaminants with the surface. A surfactant package (which can be a combination of more than one surfactant) can use a nonionic surfactant, or can use an anionic or cationic surfactant or an amphoteric surfactant or a mixture comprising various different surfactants. Examples of surfactants that can be used include sodium dodecyl sulfate; alkyl ethoxylates; amine oxides; amphoteric betaines; alkyl sulfonates; alkyl phenosulfonates; fluorosurfactants; and the like. Sodium dodecyl sulfate (SDS), which is an anionic surfactant, is known to penetrate and help dislodge biofilm. Other surfactants can be used to make the compositions of invention without limitation as provided for example in Milton J. Rosen Monograph "Surfactants and interfacial phenomena", third edition, Wiley Interscience (2004), and in "Surfactants—A Practical Handbook", Edited by K. Robert Lange, Hanser Publisher, Munich (1999).

Suitable anionic surfactants include fatty acid soaps covering a range of alkyl chain length, for example up to about 18 carbon atoms, and may be straight or branched chain alkyl groups. These surfactants are normally used at a pH higher than the dissociation constant of their corresponding carboxylic acid. Another class of anionic surfactants that has been found to be effective with the present method is alkyl sulfates and sulfonates, such as SDS. Another useful anionic surfactant may be based on alkylpolyoxyethylene sulfate. Another anionic surfactant that can be used is an alkylbenzene sulfonate. Linear and branched chain alkylbenzene sulfates with one or more sulfonate groups have been found to be useful. Suitable anionic surfactants also include alpha-olefin sulfonates, monoalkyl phosphates, acyl isothionates, acyl glutamates, N-acyl sarcosinates and alkenyl succinates and the like that have an anionic surface group and possess surface activity.

Suitable amphoteric surfactants include for example alkyldimethylamine oxides, alkylcarboxy betaines, alkylsulfobetaines, amide-amino acid type amphoterics and others that may exhibit amphoteric and surface activity. Amphoteric substances have characteristics of both acid and alkali groups.

Useful nonionic surfactants include for example polyoxyethylene alkyl ethers, polyethylene alkylphenyl ethers, polyethylene fatty acid esters, sorbitan fatty acid esters, polyethylene sorbitan fatty acid esters, sugar esters of fatty acids, alkyl polyglycosides, fatty acid diethanolamides, fatty acid monoglycerides, alkylmonoglyceral ethers, fatty acid polypropyleneglycol esters and the like.

Useful cationic surfactants include for example alkyltrimethylammonium salts and their phosphonium analogues, dialkyldimethyl ammonium salts, alkylammonium salts, alkylbenzyldimethylammonium salts, alkylpyridinium salts and the like which bear cationic functional groups and possess some surface activity.

Polymeric dispersants can also be used. Although they do not have the molecular structure of a typical surfactant, they have similar effects. These include formaldehyde condensates of naphthalene sulfonate, sodium acrylates or copolymers of other acrylic acids, copolymers of olefins and sodium maleate, lignin sulfonates, polyphosphates, silicates and polysilicates, carboxymethyl cellulose, cationic cellulose, cationic starches, polyvinyl alcohol, polyethylene glycol, polyacrylamides, polyethylene oxide/polypropylene oxide block copolymers (e.g., di- and tri-block), and the like. These compositions are also useful herein to function substantially as surfactants. There are also detergent substances which are not strictly surfactants. Examples include trisodium phosphate, sodium carbonate and polymers. Such substances can also be used with the present invention.

Solvents, Cosolvents

The carrier fluid or vehicle for the gel or Minute Fibrils, such as an aqueous carrier fluid, can comprise an organic solvent and optionally can further include a co-solvent. A co-solvent is a second solvent added in a smaller quantity than the primary solvent to enhance the dissolving ability of the primary organic solvent. The solvent and optionally the co-solvent can help to remove substances such as protein or organic soil. Organic soil can be protein, lipids, carbohydrate, hemoglobin or similar substances. The solvent and the optional co-solvent can be for example propylene glycol or a glycol ether. Solvents such as propylene glycol and glycols ethers (from e.g., DOW Chemical Company) and others can be useful in the compositions of the invention because they contribute to achieving high-level removal of lipids and some proteins from endoscope channels and from external surfaces of medical or industrial devices.

The term propylene glycol is intended to refer to any enantiomer or isomer of propylene glycol, either alone or in combination. This includes α-propylene glycol (propane-1, 2-diol) and β-propylene glycol (propane-1,3-diol). Propylene glycol is highly miscible with water and also is able to dissolve various organic substances.

Glycol ethers are a group of solvents (often termed "cleaners") based on alkyl ethers of ethylene glycol or propylene glycol. Most glycol ethers are water-soluble. They are also able to dissolve various organic substances. As non-limiting examples, glycol ethers include at least the following substances: Ethylene glycol monomethyl ether (2-methoxyethanol, CH3OCH2CH2OH); Ethylene glycol monoethyl ether (2-ethoxyethanol, CH3CH2OCH2CH2OH); Ethylene glycol monopropyl ether (2-propoxyethanol, CH3CH2CH2OCH2CH2OH); Ethylene glycol monoisopropyl ether (2-isopropoxyethanol, (CH3)2CHOCH2CH2OH); Ethylene glycol monobutyl ether (2-butoxyethanol, CH3CH2CH2CH2OCH2CH2OH); Ethylene glycol monophenyl ether (2-phenoxyethanol, C6H5OCH2CH2OH); Ethylene glycol monobenzyl ether (2-benzyloxyethanol, C6H5CH2OCH2CH2OH); Diethylene glycol monomethyl ether (2-(2-methoxyethoxy)ethanol, methyl carbitol, CH3OCH2CH2OCH2CH2OH); Diethylene glycol monoethyl ether (2-(2-ethoxyethoxy)ethanol, carbitol cellosolve, CH3CH2OCH2CH2OCH2CH2OH); and Diethylene glycol mono-n-butyl ether (2-(2-butoxyethoxy) ethanol, butyl carbitol, CH3CH2CH2CH2OCH2CH2OCH2CH2OH). The commercial product Carbitol™ (The DOW Chemical Company) is a glycol ether, Diethylene Glycol Monoethyl Ether, which can be used as a co-solvent.

Other solvents and co-solvents beyond those named can also be used, such as esters or ketones (such as water-soluble such compounds), and alcohols.

In embodiments, the solvent is not primarily aqueous.

pH Adjustment

In embodiments of the invention, the composition can include an additive that adjusts the pH of the composition in a desired direction. Examples of substances that can adjust the pH of a solution in the alkaline direction include sodium hydroxide, sodium phosphate and sodium metasilicate. For adjusting the pH of the solution in the acidic direction, HCl or other organic or inorganic acids can be used, thereby providing compositions of lower pH. A pH range between about 3 to 11.5 can be useful for the formulations of invention. A basic or acidic range can be chosen in light of anticipated contaminants A cleaning cycle with one pH can be followed with one configured for another pH. A pH range between 7 and 11 can be favorable for cleaning of endoscopes and similar devices. A composition of any desired pH can be formulated and used depending on the surface and on the contaminants to be cleaned.

Buffers

In embodiments of the invention, the composition can include an additive to help maintain a desired pH of the composition. Appropriate buffering additives can include acetate, citrate, phosphate, tris-buffer and other known buffers as is known in buffering systems in chemistry and biology. Other buffering systems, especially bicarbonate and phosphate, are also suitable in the compositions of the invention. Phosphate can be used to keep the pH of the composition between 7 and 11, which may be favorable for cleaning of endoscopes and similar devices. A buffer based on sodium hydroxide and tri-sodium phosphate can also be used to make the carrier fluid.

Builders and Chelating Agents

In embodiments of the invention, the composition can include chelating agent(s) that can sequester calcium and other multivalent cations that can stabilize built-up solid matter. This can help in killing bacteria and in facilitating cleaning especially if the water used has some hardness or containing multivalent cations such as calcium. Removing Calcium can disrupt cell walls, which in turn can make the contaminant easier to remove. Removing calcium also can prevent the formation of scale if tap water is used for certain processing steps later. Examples of such a chelating substance include EDTA (ethylenediamine tetra acetic acid); tetra sodium ethylene diamine tetraacetic acid (available commercially as Versene™ from DOW Chemical Company); sodium metasilicate; phosphates including polyphosphates; and similar substances. The compositions can include builders, similar to chelating agents that sequester ions such as calcium or magnesium ions. An exemplary builder is sodium tripolyphosphate (STPP).

Antimicrobial Agents and Antibiotics

In embodiments of the invention, the liquid composition can include an antimicrobial additive. It should be understood that the term antimicrobials is intended to include any one or more of various categories of substances, such as antimicrobials, antiseptics, disinfectants, biocides, antibiotics, virucides, prion-inactivating agents, antifungals, antiparasitics, and the like. Antimicrobial substances include drugs, chemicals, or other substances that either kill or slow the growth of microbes. The category also includes any of a large variety of chemical compounds and physical agents that are used to destroy microorganisms or to prevent their growth or development.

Alcohol, and alcohol in combination with other compounds, is a class of proven surface sanitizers and disinfectants. A mixture of 70% ethanol or isopropanol diluted in water is effective against a wide spectrum of bacteria. The synergistic effect of 29.4% ethanol with dodecanoic acid is effective against a broad spectrum of bacteria, fungi, and viruses. Sometimes an alcohol can be combined with a quaternary ammonium antimicrobial such as is described herein.

Another category is aldehydes, such as formaldehyde, glutaraldehyde, or ortho-phthalaldehyde. These compounds have a wide microbiocidal activity and are sporicidal and fungicidal.

Agents such as chlorine and oxygen that are strong oxidizers, are widely used for antibacterial purposes. Examples of such oxidizing agents include: sodium hypochlorite (commonly known as bleach), one of whose precursors is dichloroisocyanurate; other hypochlorites such as calcium hypochlorite (it can be noted that hypochlorites yield an aqueous solution of hypochlorous acid that is the true disinfectant, with hypobromite solutions also being used sometimes); electrolyzed water or "Anolyte," which is an oxidizing, acidic hypochlorite solution made by electrolysis of sodium chloride into sodium hypochlorite and hypochlorous acid (the predominant oxychlorine species being hypochlorous acid); chloramine, which is often used in drinking water treatment; chloramine-T (which is antibacterial even after the chlorine has been spent, because the parent compound is a sulfonamide antibiotic); chlorine dioxide (with sodium chlorite, sodium chlorate, and potassium chlorate being used as precursors for generating chlorine dioxide); hydrogen peroxide (which is used in hospitals to disinfect surfaces and it is used in solution alone or in combination with other chemicals as a high level disinfectant; is sometimes mixed with colloidal silver); iodine, sometimes in the form of tincture of iodine, or alternatively a commercially available product known as Povidone-iodine; peracetic acid, which is a disinfectant produced by reacting hydrogen peroxide with acetic acid; performic acid, which is the simplest and most powerful perorganic acid; other perorganic acids; potassium permanganate (KMnO4); and potassium peroxymonosulfate.

Quaternary ammonium compounds, sometimes referred to as "quats," are a large group of related compounds. These substances are biocides that also kill algae. Examples include benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. Biguanide compounds, including chlorhexidine (CHX) and polyhexamethylene biguanide (PHMB), represent another class of cationic antimicrobial compounds that are effective against a wide spectrum of organisms. Specifically, biguanides are attractive antimicrobials for use in the present invention because resistant strains have not appeared since their discovery more than 50 years ago.

Phenolics are active ingredients in some household disinfectants, some mouthwashes and in disinfectant soap and handwashes. They include the following substances: phenol (formerly called carbolic acid); o-Phenylphenol, which is often used instead of phenol, since it is somewhat less corrosive; Chloroxylenol; hexachlorophene; thymol (a phenolic chemical found in thyme); amylmetacresol; and 2,4-dichlorobenzyl alcohol.

Still other known antimicrobial substances include: silver dihydrogen citrate (SDC), which is a chelated form of silver that maintains its stability; biguanide polymer; polyaminopropyl biguanide; sodium bicarbonate (NaHCO3), which has antifungal properties; lactic acid; copper-alloy surfaces. In the 1940s and early 1950s, studies showed inactivation of diverse bacteria, influenza virus, and Penicillium chrysogenum (previously P. notatum) mold fungus using various glycols, principally propylene glycol and triethylene glycol.

Antibiotics including all classes [see e.g. Anthony R M Coates, Gerry Halls, and Yanmin Hu, "Novel classes of antibiotics or more of the same?", Br J Pharmacol. 2011 May; 163(1): 184-194] can also be used as antimicrobial agents in the compositions of the invention.

Viscosity Modifiers and Gel-Forming Substances

In embodiments of the invention, the composition can include a gel forming substance or a viscosity modifier. For example, a Minute Fibril formulation can be further modified with a gel forming substance (not comprising Minute Fibrils) or a viscosity modifier.

A viscosity modifier can be a substance that, when dissolved in water or an aqueous solution or a carrier fluid used in the invention, increases the viscosity. Examples of such substances include: carboxymethyl cellulose, hydroxyethylcellulose; hydroxy propyl methyl cellulose; polyvinyl alcohol; polyvinyl acetate copolymer; polyvinyl pyrrolidone; and the like. Such additives can increase the viscosity of water from its ordinary value of approximately 1 centipoise to a value in the range of 500 to 10000 centipoise (mPa·s) or more. Such property can also work as a suspending agent to prevent possible separation of components, provide stability, and provide a composition with a longer shelf life. Other polymers that can increase the yield shear stress and stiffness of the gel network such as carbopols and the like can also be used as described elsewhere herein In embodiments of the invention there can be provided gels, which can be homogeneous gels (without fibers or Minute Fibrils), which can be hydrogels. Such gels provide a viscosity greater than the viscosity of water such as in the range between 100 to 10,000 centipoise or higher. For a description such as this, realizing that for a non-Newtonian fluid the viscosity is a function of shear rate, the viscosity discussed can be an average or effective viscosity at conditions of interest for cleaning applications. Such viscosity can be the value of the viscosity that, when used in the Hagen-Poiseuille Law, best correlates an observed volumetric flowrate and an observed pressure drop. A homogeneous composition can be made with small molecular weight viscosity enhancing compounds such as glycerol or sugars, or from macromolecules either cellulosic or non-cellulosic, or from inorganic gel forming substances such as silica or clays including laponite, hectorite, bentonite or others. Such gels, even if they do not contain solids or fibers (as described elsewhere herein), can have usefulness for decontamination. Compositions based on homogeneous gels can be for storage of a medical device or an article, as discussed in various places herein. Also, such gels can have some usefulness for cleaning as described elsewhere herein.

A factor that can influence the choice of a gel forming agent or viscosity modifier is the ease with which that substance can be rinsed from the channel after residing in the channel. Some gel-forming substances are very soluble in water, which contributes to their ability to be rinsed out. For example, polyethylene oxide (PEO) and polyethylene glycol (PEG) of intermediate or high molecular weight are highly water-soluble and are easy to rinse out. As long as such compositions can hold a sufficient amount of various additional substances, they can be useful according to embodiments of the invention.

Hygroscopic Additives

In embodiments of the invention, especially if a composition is intended to remain inside a passageway of a medical device, or in contact with a surface, for an extended period of time (e.g., for storage), the fluid composition can be hygroscopic or can contain a humectant, so as to inhibit drying over extended periods of time. Drying can increase the adherence of contaminants. Hygroscopic or humectant additives include: propylene glycol; hexylene glycol; butylene glycol; glyceryl triacetate; neoagarobiose; sugar alcohols (sugar polyols) such as glycerol, sorbitol, xylitol, maltitol; and the like. Some substances that serve as viscosity modifiers or gel formers can also serve this purpose. Other hygroscopic additives include: polyvinyl alcohol; polyethyleneglycol; hydroxypropylmethylcellulose; polyacrylic acid (available as Carbomer®); polyvinyl pyrrolidone.

These substances are hygroscopic as well as hydrophilic. There is a tendency for hydrophilic substances to also be hygroscopic to at least some extent.

Preservative

In embodiments of the invention, the composition can include a preservative, especially for some of the compositions. For example, it can be appropriate to include a preservative in compositions that contain ingredients such as guar gum, xanthan gum, carrageenan, or other substances which could support the growth of bacteria. Such a preservative can for example be sodium benzoate, benzoic acid, methyl paraben or other preservative compounds at concentrations that prevent growth and provide a product shelf life of about one year or more.

Adjuvants

Compositions of embodiments can include a number adjuvants (color, preservative, suspending agent, flavor, and others as known in the art). Appropriate additives for these purposes can be used.

Taking into account the just-described types of additives and ingredients, following are some possible formulations of carrier fluids, more specifically aqueous carrier fluids that can be used in embodiments of the invention.

Exemplary Carrier Fluid 1

Recited in Table 4 is an exemplary carrier fluid, which may be referenced as "CS-19."

TABLE 4

| Component | Conc., g/L | Function or category of substance |
|---|---|---|
| NaOH | 0.48 | pH adjustment agent |
| Tetrasodium pyrophosphate | 15 | Suspending agent |
| SMS sodium metasilicate | 3 | Increases pH, chelating agent |
| Ethylenediaminetetraacetic acid(39%) | 23.1 | Ca sequesterant, tetrasodium EDTA |
| Accusol 445N | 15 | Dispersant polyacrylic dispersant |
| Dehypound Advanced | 6 | Surfactant nonionic low foaming |
| Dehydol OD 5 | 1.5 | Co-surfactant that functions synergistically with the first surfactant |
| 1,2 Propanediol | 2.5 | Organic Solvent for facilitating removal of oily contaminants |
| Triethanolamine | 5 | Adjuvant and pH adjustment |

ACUSOL 445N is a homopolymer of acrylic acid with an optimized molecular weight to be used in applications such as: liquid fabric wash, laundry additives, industrial and institutional detergents (Rohm and Haas Company, Philadelphia, Pa.). Dehypound Advanced is believed to be Caprylyl Glucoside and Decyl Glucoside and Deceth-5 and PPG-6-Laureth-3 (BASF Corporation, Florham Park, N.J.). Dehydol is a laureth-4 polymer used as a nonionic emulsifier (BASF Corporation, Florham Park, N.J.).

Exemplary Carrier Fluid 2

Recited in Table 5 is an exemplary carrier fluid, which may be referenced as "Modified CS-19."

TABLE 5

| Component | Conc., g/L | Function or category of substance |
|---|---|---|
| NaOH (50% by weight solution) | 0.08 | pH adjustment agent |
| Tetrasodium pyrophosphate | 2.5 | Suspending agent |
| SMS sodium metasilicate | 0.5 | Increases pH, chelating agent |
| Versene (39%) | 3.85 | Ca sequesterant (tetrasodium EDTA) |

TABLE 5-continued

| Component | Conc., g/L | Function or category of substance |
|---|---|---|
| Accusol 445N | 2.5 | Dispersant polyacrylic dispersant |
| Dehypound Advanced | 1 | Surfactant nonionic low foaming |
| Dehydol OD 5 | 0.25 | Co-surfactant that functions synergistically with the first surfactant |
| 1,2 Propanediol | 20.42 | Organic Solvent for facilitating removal of oily contaminants |
| Triethanolamine | 0.83 | pH adjustment |
| 1 Methyl-2 Pyrrolidone | 10.0 | Cosolvent/cleaner |
| Glycol Ether (DPM) | 10.0 | Solvent/cleaner |

DPM is Dipropylene Glycol Methyl Ether CH3O[CH2CH(CH3)O]2H (One of several isomers) (obtained from Dow Chemical).

Rinsing

Rinsing can be performed with water that is warm, preferably at about 30° C. to about 45° C. In embodiments of the invention, rinsing can be performed with water or aqueous composition that is sterile or free of bacteria and organisms. Such water or aqueous composition can be produced by filtration or it is possible to use a small concentration of antimicrobial disinfectant or sterilant, for example such as a low concentration of peracetic acid. Rinsing can be performed with water that is deionized, produced by reverse osmosis or produced by distillation, etc. During a rinsing process, a real-time testing procedure can be used to determine when adequate rinsing has been achieved, including spectroscopic methods, conductivity, special test strip, surface tension or other appropriate methods testing the composition of the liquid exiting from the device. Testing can be for the polymer components of the cleaning composition.

In past work by some of the same inventors as listed on this patent application (such as U.S. Pat. Nos. 6,454,871 and 6,857,436 and 8,226,774), it has been demonstrated that two-phase liquid-gas flow is effective for removing such polymeric material from narrow channels. In such a procedure, a typical ratio of liquid to gas, on a volumetric basis, that can be used is about 1:1000. In general, for a common set of conditions such as maximum allowable pressure drop across a flowpath, two phase flow is capable of much better cleaning than simple liquid flow. Thus, if needed, two-phase flow can be utilized.

For rinsing, turbulent flow can be utilized. After rinsing, alcohol and then air can be passed through the channels to dry them. It can be assumed that the turbulent regime exists at a Reynolds number of greater than approximately 2000, although there is known to be a transition region in the vicinity of that number.

For purposes of determining the Reynolds number, the velocity used in calculating the Reynolds Number would be a bulk velocity (volumetric flowrate divided by cross-sectional area), and the viscosity used would be a viscosity that, when substituted in the Hagen-Poiseuille equation, correlates the observed volumetric flowrate with the observed pressure drop. The viscosity of the cleaning composition will likely be much larger than the viscosity of the rinsing composition as described elsewhere herein. The rinsing composition may have a viscosity that is similar to the viscosity of pure water. For an endoscope channel having passageways along its length, the selection of flow conditions for both cleaning composition and rinsing composition will likely be influenced by a need to stay within an overall pressure drop across the length of the passageway which is typically about 2-3 atmospheres. It is possible that the flow of the cleaning composition may be laminar because of the typically large viscosity of the cleaning composition. It is believed that the use of turbulent flow during rinsing may be helpful if the geometry of the passageways has geometric irregularities such as expansions or branches. For example, such irregularities may be places where it is especially difficult to adequately rinse out the cleaning composition. It is believed that with turbulence, the flow of the rinsing composition may spread more thoroughly and quickly into irregular geometries, thereby producing better rinsing. Currently the profession does not appreciate the importance of turbulent flow and turbulent mixing during rinsing.

Optional Minimization of Lubricious Substances

In certain embodiments it can be appropriate to be judicious with substances that have the property of being lubricious when in their pure or nearly-pure form. Although it is common to think of oily substances as being lubricious, additional substances can be lubricious, including water-soluble or water-miscible substances to be lubricious. A lubricious substance may lessen the probability of a fibril or an abrasive particle coming into contact with a surface that is desired to be cleaned, and such lessening of contact may lessen shear or abrasive action acting on a contaminant. Substances for which the amount can be limited to less than lubricious amounts can include: glycerol; glycerol esters; glycerol oleate; glycerol stearate; carboxymethyl cellulose; hydroxypropylmethylcellulose; propylene glycol; esters of fatty acids; long-chain hydrophobic surfactants; sodium laureth sulfate; behentrimonium chloride/amodimethicon; simethicone; and other silicone compounds.

Shear Thinning and Substantial Plug Flow

Figure 3:
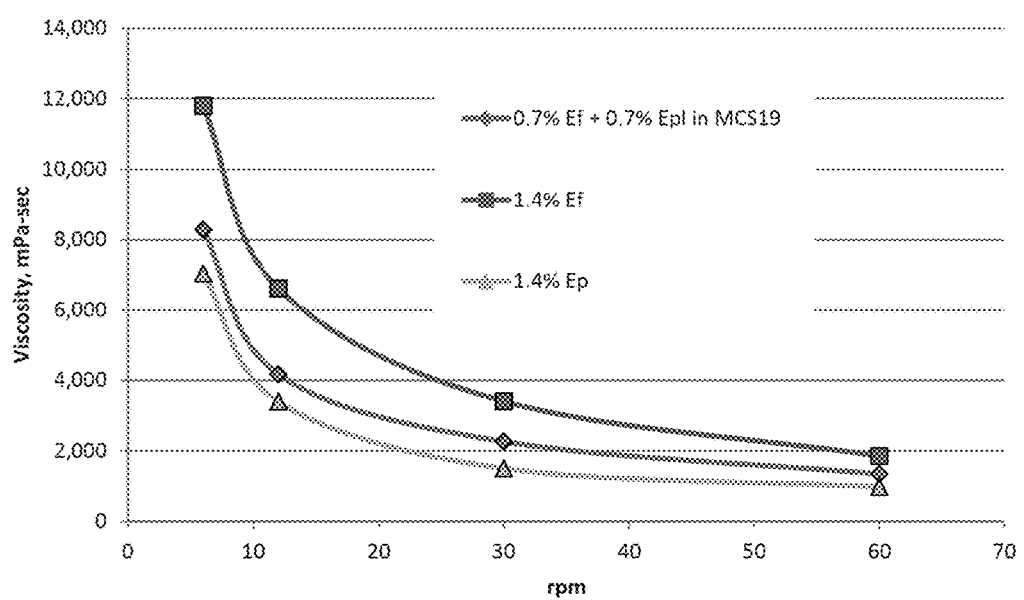
FIG. 3 shows shear thinning behavior during dynamic viscosity measurements.

Shearing thinning useful in the invention is illustrated by FIG. 3, wherein the viscosity of various aqueous compositions of 1.4% w/w cellulosic Minute Fibrils (of Exilva Forte (Ef), Exilva plano (Ep) and Exilva plano light (Epl), as indicated in the Figure) is shown as a function of the rpm of the paddle used in the testing device. The testing device used is an Anton Parr Physica Model 501 Rheometer.

In embodiments, the cleaning compositions show shear thinning from 5 rpm (shear rate of 3.33/sec) to 30 rpm (shear rate of 20/sec) by a viscosity reduction factor of about 2-fold or more, or by about 3-fold or more, or by about 4-fold or more.

Figure 4:
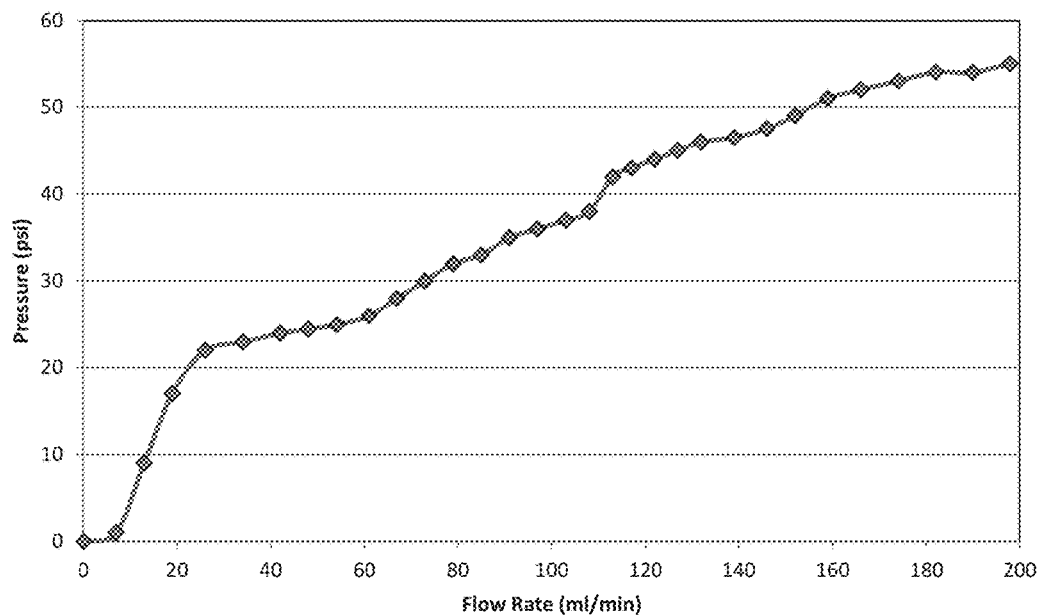
FIG. 4 shows pressure vs. flow rate for a narrow channel.

In FIG. 4, there is a sharp decrease in slope for the pressure seen at a flow rate of about 20 mL/min. The test was for a 1.4% composition of Exilva forte pumped through a 12 ft. length of 3.2 mm ID PTFE tubing. The figure shows, starting from the origin and for a certain range (here, to about 20 mL/min), the pressure drop rises monotonically with flowrate. Then, above a certain flowrate, there can be reached a sort of plateau, or at least a region in which the increase is not so rapid (here, about 22 mL/min to about 58 mL/min). Then, above a still larger flowrate, the pressure drop again increases with flowrate, or increases more steeply than in the plateau region. The details of such a characteristic can vary with the composition. It is believed, although it is not wished to be limited to this explanation, that the first region corresponds to what might be called plug flow, in which the network in the central part of a cross-section remains largely intact, and shear and disruption of the network occurs mostly near the wall or boundary. The plateau region of the characteristic is believed to correspond to a situation in which disruption of the network occurs more widely. It is believed that the third region of the characteristic corresponds to a situation in which the network is fully disrupted. One can obtain useful cleaning in the other regions, but cleaning seems to be more efficient in the first or plug flow region.

Yield Shear Stress—Elasticity

The rheology of a viscoelastic material can be described by a complex modulus. Rheometry equipment for use with this invention applies an oscillatory stimulus to the material, and measures response in terms of both amplitude and phase angle. This can measure a complex modulus, which can be divided into two parts. The complex modulus contains the storage modulus G', which describes the elastic properties, and G", the loss modulus, which describes the viscous properties. Both quantities have units of Pascals or similar units. The storage modulus G' is like an elastic modulus in a situation of elastic deformation. The loss modulus is related to viscosity in a flow situation. The measurement further yields the yield shear stress. An Anton Paar Physica RM 501 Rheometer operating with a 25 mm and a 50 mm parallel plate at 1 mm or 2 mm gap distance is used. G' and G" measurements were performed as a function of strain rate in rad/s. In addition, amplitude sweeps were performed as a function of shear stress (Pa). All measurements are made at room temperature.

Without being bound by theory, Applicant posits that a composition with a high storage modulus G' will have greater cleaning efficiency. Accordingly, storage modulus G' of at least in the tens of Pa, and perhaps in the hundreds of Pa (such as 200 Pa) or even higher, is desirable. It is proposed that if the storage modulus G' or the yield shear stress of the composition is larger than the modulus of the contaminant (which is believed to be in the single digits of Pa or low tens of Pa for traditional biofilm, and in the tens of Pa for BBF), the cleaning efficiency will be higher. It is further proposed that it is desirable that the storage modulus G' of the composition is larger than the loss modulus G". Not wishing to be bound by theory, the stiffness (G' or elastic modulus) and strength of the gel network (yield shear stress) need to be larger than that of the biofilm in order to achieve its removal. Literature data indicate that G' of biofilms can range from less than 100 Pa to more than 2000 Pa (Stoodley et al., Biotechnol Bioeng. 1999 Oct. 5; 65(1):83-92). For example, the storage modulus can be 200 Pa or higher, measured at 0 rads/s.

For a material that has a yield shear stress, it can be envisioned that in an open-topped container of the material, a load can be applied to a portion of the exposed surface, and up to a certain load, the surface of the material will deform simply in an elastic manner without the applicator breaking through the surface. At a sufficiently large load, the load will penetrate through the exposed surface of the material and will travel creating a pattern of flow around the applicator of the load. The load at which the behavior changes from elastic deformation to flow corresponds to the yield shear stress. For a material that has a yield shear stress and contains a network of entangled fibrils, it is believed that the measured yield shear stress is descriptive of the strength of the network of entangled fibrils. The storage modulus describes yield shear stress the elastic properties or stiffness of the network.

Minute Fibril compositions can produce a network structure having significant yield shear stress at relatively low concentrations/consistency. The yield shear stress is an indication of the strength of the network. Yield shear stress vs. weight % of Exilva (Borregaard) in water is given in Table 6. The yield shear stress exhibited by inventive compositions is believed to arise from fiber or fibrillated entities entangled or crowded or connected to together in the network. This network can be broken up or destroyed at higher shear rates or when the shear stress exceeds the yield shear stress forming flocs and network fragments. The actual mechanisms regarding breakdown of network are not clearly understood and we do not wish to be bound by theory.

The ability to develop networks that have yield shear stress in the range between about 0.1 to 100 Pascal and preferably between about 5 or about 20 Pascal to about 50 or about 60 Pascal can be useful for producing cleaning compositions that are predisposed to be retained in a channel for a period of time, and, at the same time be thereafter readily discharged and thoroughly cleared from the channel due to a shear-thinning character (which can be strong). Networks with higher yield shear stress from about 10 to 60 Pa can possess reasonable strength such that during flow they can make contact with contaminants at the tube wall and effect the removal of the contaminants from the channels. Yield shear stress is considered a parameter that can predict the extent of entities making contact with channel surface during cleaning. It can be seen in Table 6 that a base concentration of Minute Fibrils can form network structures that have a yield shear stress favored for such embodiments involving retention and flow. For certain embodiments, a yield shear stress for the composition of between about 0.1 or 1.0 Pa and about 200 Pa is useful, and in other embodiments between about 5.0 or about 20 Pa and about 60 or about 100 Pa is useful.

TABLE 6

| Concentration of Exilva Forte (w/w) | Yield Shear Stress, Pa |
|---|---|
| 0.1% | 0.03 |
| 0.5% | 0.3 |
| 1.4% | 41 |

The yield shear stress is preferably high enough such that a plug flow can occur without destroying the network. However, the yield shear stress alone as determined by a rheometer might not fully predict the ability to make a network (for purpose of creating entanglement) or even more specifically to flow in a favored plug regime.

In embodiments, such as above 1% concentration of minute fibrils by weight, the G' values were higher than G" which implies that these gels behave as an elastic solid. Network gels formed at higher concentrations (>1.2% minute fibrils by weight) have considerable stiffness and yield shear stress due to considerable fiber-fiber contacts and entanglements of fibrillated entities.

As elucidated further in the Elasticity and Stiffness Appendix to Provisional B (identified below), it is believed that the strength of individual fibers determines the overall stiffness of the gel if no bundling is present. If bundling or aggregation is present, the spring constant of the bundle is observed to be strongly dependent on the inter-fiber bonding. If fibers form bundles with strong inter-fiber bonds, all fibers in the bundle behave as a continuous elastic material and the bending modulus of the bundle scales with the fourth power of the bundle diameter. If such a strong bonding is not present, the fibers behave as individual elements and the scaling of the bundle bending modulus merely goes as proportional to the square of the bundle diameter (asymptotically). Under mechanical deformation fibers and sub-groups of fibers may emerge, resulting in a mixture of bonded and unbonded sub-bundles. In such a case, the bending modulus of the bundles is dependent on the bundle diameter as where the scaling of the elasticity with bundle diameter is not directly related to the scaling with concentration. Accordingly, the elasticity of the network can be tailored by selecting the minute fibril material concentration and properties including dimensions of fibers or fibrils, interaction or bonding due to fiber-fiber contact and entanglement. In embodiments, the elasticity of the gel network composition can be adjusted by using a mixture of minute fibril materials and by the addition of stiffening elements of different dimensions and elastic moduli (e.g., microcrystalline cellulose or the like) or combinations thereof. Accordingly, one skilled in the art can employ embodiments of the invention to make a range of compositions having different properties to employ in different applications as desired. Hence, the invention is not meant to be limited to the exemplified materials described herein.

In additions to the mechanical properties of individual fiber and fibrils, inter-fiber interactions including fiber-fiber contacts and entanglements contribute to the gel network stiffness. MacKintosh et al., Phys. Rev. Lett., 1995, 75, 4425-4428 have predicted the dependence of stiffness on the concentration of the fibers forming a network. The dependence of stiffness on parameters other than concentration such as the fiber-fiber contacts, entanglements and added stiffening elements need to be considered to describe the gel networks of the invention. On the basis of SEM micrographs and scaling of elasticity with concentration, a model based on rod network may be valid. In such a model, the stiffness depends on many factors including the bending springe constant of individual fibers.

Boundary Floc Surface Collisions

Applicant has undertaken rough estimations of the number of collisions between a floc of Minute Fibrils and the surface of a channel, and has calculated that this can be 10,000 collisions between a given boundary floc and the surface as the boundary floc travels 1 meter. Calculations of this type are presented in Provisional Patent Application U.S. Ser. No. 62/402,394, filed Sep. 30, 2016 ("Provisional A"), and Provisional Patent Application U.S. Ser. No. 62/563,975, filed Sep. 27, 2017 ("Provisional B," together, the "Provisionals"). Further such modeling posits that the formation of a thin gap between contaminant particle and fiber portion nearest to the wall is sufficient to remove the contaminant because the local shear rate (shear stress) within this gap can exceed the shear rate averaged over the wall surface in orders of magnitude. Based on such modeling, the local shear stress within the gap can be for example about 30 times larger than the average bulk shear stress. This modeling is outlined in the Provisionals.*** The modeling posits that flocs on the interior of the network (colliding flocs) collide with boundary flocs, increasing the surface collisions, and helping to overcome the depletion layer effect that protects channel walls from effects of fluid flow.

Biofilm that is attached to a surface can be described by a shear stress that the biofilm can withstand before becoming detached from the surface. It is believed that the shear strength of traditional biofilm (not crosslinked) is in the range of 5 to 20 Pa, and a shear strength of BBF is in the range of 10 to 50 Pa. It is further believed that the compositions of the invention can achieve bulk and localized yield shear stress and forces created during flow that are greater than or approximately equal to the shear strength of biofilm, encouraging fragmentation and detachment of the biofilm. While it is believed that the local shear stress can rise to values much higher, it is believed that the bulk shear stress provides a good rule of thumb on effectiveness of a composition for removing a given material. Through adjustments of composition, compositions can be formulated that have high yield shear stress, such as in the range of from about 1 to 100 or 200 Pa, or about 5 Pa to about 50 Pa.

As also modeled in the Provisional, the Treatment Number, TN, predicts the number of tube surface treatments (the number of times that any given area is contacted by Boundary Flocs) during flow. If Treatment Number TN is <1, the cleaning is likely not sufficient. A many-fold tube treatment by fibers can be achieved during our cleaning with the flow of a gel that comprises Minute Fibrils. This explains why a high level of cleaning can take place. With parameters much like described here, the Treatment Number can be in the range of 100 to 10,000 depending on the number of volume changes and dimensions of flocs and their contact area with the tube wall. In an embodiment of the invention, a calculated Treatment Number of more than 1 is desirable, and for achieving high-level cleaning, a Treatment Number of greater than about 25, 50 or 100 is useful.

Additional Operational Parameters for Channel Cleaning

In embodiments, the composition can be caused to flow as a relatively intact fibrillated network at low velocities or low shear rate so that a plug-like flow is realized and the network can be intact or nearly intact near the wall of channel. As such the flocs or fibrils at the boundary of the flowing network are believed to touch and make some form of contact with the surface of the channel or passageway and remove contaminants by direct or indirect action involving desorption, detachment, sequestration or incorporation in the network and transfer of entrapped contaminants along with network to the exit of the channel or passageway. Without being bound by theory, it is believed that the action of cleaning or removal in this case can involve direct contacts with the surface or by indirect generation of high shear stresses near the surface of the channel causing detachment and removal of contaminants. In embodiments, the linear velocity of plug networks is diagnostic of cleaning efficacy. Exemplary linear velocities found favorable include those about 1.0 cm/second to about 10 cm/second. Higher linear velocity of gel network in a regime where the network remains intact or nearly intact during flow is preferred because this provide shorter cleaning time. Not being bound by theory, the highest possible linear velocity of gel network that can produce contact or near contact with the wall is generally preferred.

The rate of cleaning can be manipulated by adjusting for example flow velocity, pressure drop and the concentration of the polymer material in the composition used. Treatment times can be as short as one minute or as long as about 30 minutes or longer depending on the nature of contaminants but in embodiments it can be between about 2 to about 10 minutes or so. Cleaning parameters can be adjusted so that the flowing network can remain intact or nearly intact at the surface as described above. Without being bound by theory, it is believed that less effective cleaning will generally be obtained as the fibrillated network degrades with higher flow rates. Although direct contact of polymer material with the channel surface may be less compared to plug-like flow of a substantially intact network, there is still significant contaminant removal and cleaning with such flocculated flow. For example loose bacteria and organic soil can be cleaned by flocculated flow due to lower strength compared to for example BBF.

The volumetric flow velocities used to remove biofilm from channels with ID between about 1.0 mm and about 4 mm are in the range of about 5 to about 70 ml/minute during the plug-like flow cleaning mode, and can be larger than this when the flow regime is flocculated or fragmented flow. The terms "flocculated flow" and "fragmented flow" are considered to be synonymous and denote conditions when the network is broken into fragments or flocs. Volumetric flow rates can even be in the range of about 100 to about 400 ml/minute depending on the channel diameter and the flow regime.

In embodiments, narrow channel internal diameters typically are in the range of about 0.6 mm to about 6.0 mm. In embodiments, narrow channels can have length in the range of about 20 to about 350 cm or more.

Compositions can be used at temperatures in the range for example of about 20° C. to about 80° C.

For embodiments where the channel to be cleaned has ID of about 2 to about 4 mm (e.g., the SB channel), the following parameters (about to about) are illustratively useful:

TABLE 7

| Flow Rate (ml/min) | Velocity (cm/sec) | Time (min) | Pressure drop (psi) |
| --- | --- | --- | --- |
| 2-4 mm Channel - Cleaning | | | |
| 12-75 | 1-5 | 5-15 | <28 |
| 2-4 mm Channel - Rinsing | | | |
| 850-1400 | 79-174 | 2 | <28 |

For embodiments where the channel to be cleaned has ID of about 1 to about 2 mm (e.g., the Air or Water (A/W) channel), the following parameters (about to about) are illustratively useful:

TABLE 8

| Flow Rate (ml/min) | Velocity (cm/sec) | Time (min) | Pressure drop (psi) |
| --- | --- | --- | --- |
| 1-2 mm Channel - Cleaning | | | |
| 8-24 | 7-21 | 5-15 | <28 |
| 1-2 mm Channel - Rinsing | | | |
| 160-170 | 140-150 | 2 | <28 |

The fibrils can have a surface charge that can be influenced or manipulated by the choice of various ingredients in the composition. If all or most of the fibrils are identically charged, they will tend to repel each other and extend away from the main fibril more than would otherwise be the case. This will effectively make the fibrillated material rougher on a very small scale, and in embodiments is believed to improve better cleaning. Carboxy methyl cellulose (CMC), or like charged polymers or particles, can provide such surface charge. For at least certain such entities, such as CMC, concentrations that provide deleterious functions, such as lubricity, are avoided. It may also be that excess concentrations can enhance a depletion layer such that the larger entities are sometimes kept away from contact with the solid boundary due to hydrodynamic lubrication forces. Concentration can be determined empirically, by testing against protein or BBF contaminants.

It is discussed elsewhere herein that the composition can contain particulate material such as MicroCrystalline Cellulose or Precipitated Calcium Carbonate, silica, or the like. It is believed that the presence of such additives increases the stiffness of the cleaning composition, compared to the same composition without such additives.

The yield shear stress Ty of a cleaning composition can be adjusted by any one or more of: adding stiffening solid additives (such as MicroCrystalline Cellulose or Precipitated Calcium Carbonate or silica); formulating a mixture of polymer and fibrillated material such as fibrillated cellulose; causing the fibrils to extend by repelling each other, such as with ionic Polymer.

Carbopol, as discussed elsewhere herein, is an additive that forms a gel that has some structure different from the structure of fibrils of cellulose or other polymers discussed herein (as seen by freeze fracture SEM). It is found that Carbopol can be used as a stiffening component so as to increase the yield shear stress of a formulation. Other polymers could also be used similarly. At the same time, any other ingredient described herein could also be used. This is an example of a fibrillated material and polymer mixture so as to provide an increased yield shear stress, an indicator of an increased strength of the fibrillated network.

Any composition described herein can contain an antimicrobial substance or an antibiotic.

Fibers can include those produced by the Lyocell process along with fibers produced by other processes. For example, a cleaning composition may comprise either or both of Exilva forte and Exilva plano lite, as discussed elsewhere herein, and may further comprise fibers produced by the Lyocell process. The Lyocell process involves extruding the material through spinnerets to form fibers. The US Federal Trade Commission defines Lyocell as a fibre "composed of cellulose precipitated from an organic solution in which no substitution of the hydroxyl groups takes place and no chemical intermediates are formed." It is believed that the fibers produced by the Lyocell process are more coarse than the fibers of the various grades of Exilva. Accordingly, the fibers produced by the Lyocell process can serve as abrading elements that are entangled within a fibrillated network formed by other fibrillated material.

Embodiments of the invention may comprise both fibrillated cellulose and fibrillated acrylic or other non-cellulosic materials.

Mixing Parameters for Composition Preparation

Non-uniform mixing of a composition can result in some regions that have a higher-than-average concentration of Minute Fibrils (or other polymer). Such local regions can pose an increased risk of clogging of small orifices or similar geometric features of the endoscope or medical device. Improper swelling and mixing of for example the Minute Fibrils in the liquid vehicle can result in large size agglomerates that can also clog small orifices during flow.

Activation of a gel refers to mixing that causes entanglement of the Minute Fibrils. As discussed elsewhere herein, it may be advantageous for there to be a considerable degree of entanglement of the Minute Fibrils with each other, which may produce a better cleaning interaction with the walls of the channel. In order to help achieve this, in embodiments of the invention, a stirring or mixing or homogenization step may be performed after initial manufacture of the composition, near in time to the use of the composition, to increase the entanglement and improve uniformity of the distribution of Minute Fibrils.

In embodiments, components of the composition are provided as separate components, to be mixed shortly before use. Mixing apparatus, which can be automated, can be provided.

Channel Bias

In certain circumstances it may be desirable to use one pump to flow composition into two or more channels. In other circumstances, the channels may have different diameters or other variations in back pressure that make it desirable to separately pump cleaning composition through individual channels.

Segmented Flow

An additional observation is that to accomplish the described cleaning, decontamination or high level disinfection, or other functions described herein, it is not essential that a fully continuous plug of the composition exist in the channel or tube, especially for situations that involve flow through the length of a narrow channel. For example, flow through the channel can be an alternating series of short segments of the composition alternating with segments of air or water. For example, if the respective lengths of the plugs and the air lengths or water lengths are approximately equal to each other, the pressure drop can be about half of what it would have been for a continuous plug of the composition. The lengths of composition segments and alternating air or water segments can be varied to achieve effective cleaning while at the same time not exceeding the pressure drop limit of the device to be cleaned, such as in the case of flexible endoscopes.

Negative Pressure

For many endoscope tubes there is a limit for allowable positive pressure that should be applied to the interior of a channel. A typical value for such a pressure limit is about 25 psig. In an embodiment of the invention, assuming that the processing is carried out in an environment of generally atmospheric pressure, a user can apply a sub-atmospheric pressure to the discharge end of the passageway while applying a source pressure at or near the pressure limit to the inlet end of the passageway. This can achieve an overall pressure drop across the passageway that is greater than the nominal pressure limit of the passageway. For example, such a negative pressure applied to the discharge end of the passageway could be approximately −10 psig, which is still not so low as to cause cavitation or boiling of water. In this way, the pressure drop from inlet to discharge of the passageway can be 25 psig—(−10 psig), or a magnitude of 35 psid. At the same time, the outward pressure experienced by the wall of the passageway is never more than 25 psid, and some portion of the wall of the passageway experiences a slight but acceptable inward pressure difference.

Medical Device Prep

Illustrative of other medical devices, endoscopes after use are subjected to a prep phase, sometimes referred to as bedside prep, intended to reduce the load of contaminants prior to more formal cleaning. The compositions of the invention can be used for this purpose. These compositions can also be added as a follow up step to more traditional prep procedures. If stored in channels of the device after prep, the compositions can decrease the chance that bacteria re-deposit on the channel walls, allowing more of the load of bacteria or other contaminants to wash out in the initial steps of more formal cleaning. Prep compositions can include an antimicrobial or antibiotic or their mixture to further suppress growth of organism or biofilms.

The gel-like or network-based composition with a yield shear stress can be retained as a body within the channel and making intimate contact with its internal surfaces. Alternatively the composition can be somewhat less gel-like such that there may be some drainage from the channel but the vacated portion of the channel is still coated with elements of the composition and thus protected from regrowth of organism or biofilm, or alternatively the composition can be still less gel-like where there is complete drainage of the composition but the channel walls are still coated elements of with the composition and thus remain protected, or alternatively the composition can be sealed in the channel by caps at the ends of the channels. For the decontamination ("prep") phase, a composition suitable for killing bacteria or other microorganisms and preventing their regrowth can be chosen. The "Prep" can include ingredients for keeping the surface wet, preventing drying and preventing adhesion of contaminants to the surface or channels during standing or waiting periods, and thus facilitating cleaning and removing during subsequent rinsing and cleaning steps. During the prep step or phase, the composition can be applied to the external confined surface of the device to prevent growth and biofilm formation and to prevent or decrease adhesion of contaminants to the surface of the device. During flow to discharge the prep composition from the channel, cleaning can also take place as well.

Device Storage

Illustrative of other medical devices, endoscopes after formal cleaning and high-level disinfection are stored in a patient-ready state. In the current invention, the devices can be stored filled with storage compositions that can be identical or similar to the compositions described here for cleaning or bedside prep. Typically they are sterile. Sterile storage fluid compositions can be used to maintain the endoscope or device in the high-level disinfected patient-ready state. The storage-decontaminating compositions can remain in the endoscope for time durations ranging from minutes to hours to days or weeks and then can be rinsed out from the endoscope or device with a sterile liquid such as sterile water, sterile saline, or the like. The intimate contact of endoscope surfaces with the decontaminating sterile storage composition can limit or prevent biofilm formation or growth during storage and thus can ensure that the endoscope is free or nearly free of organisms when it is used to treat patients after the storage composition is flushed out of the endoscope using a sterile solution.

A discovery applicable to storage embodiments, but also to cleaning protocols, is that treatment with flow of the polymeric compositions of the invention, then leaving them in place for e.g., 8 hours further loosens biofilm. Thus, a cleaning protocol may call for flow to stop for about 1, 2, 4, 8 or more hours, then resume.

In embodiments of the invention, the endoscope or device can be processed using application of sequence of compositions starting with the bedside prep followed formal cleaning with the minute fibrils composition and finally with the storage composition after completing high-level disinfection. Other sequences can be used for example the endoscope can be treated with bedside prep composition followed by cleaning with the minute fibril composition only followed by high-level disinfection or sterilization. Other sequences are envisioned where cleaning with the minute fibril composition is applied without the bedside prep and then followed by high-level disinfection or sterilization. One skilled in the art can devise other schemes to obtain the desired result depending on the device under consideration.

Oral Use

In an embodiment, the Minute Fibril composition is used for removing dental biofilm and dental plaque from teeth or oral cavity. Particles including for example silica, calcium carbonate, calcium phosphate or microcrystalline cellulose can be added as outlined herein. The compositions comprise an effective base material to make a new class of dentifrice (tooth paste), which can be specifically tailored for removing dental biofilm, plaque and preventing gingivitis. The network compositions of the invention are different from current toothpaste formulation/base in that they possess a network structure that has sufficient strength to make contact with tooth surface during brushing. The stiffness of the network can in embodiments be adjusted so that the storage modulus can be more than about 2000 Pa or more than 4000 Pa since the G' of *S. mutans* can be in this range as measured in the literature [Vinogradov et al., Biofilms, 2004, 1, 49-56]. This range of stiffness can be achieved by inclusion of stiffening additive such as microcrystalline cellulose in the composition as described elsewhere herein. The composition of the embodiments includes sufficient abrasion properties to achieve effective dental biofilm removal according new mechanisms and methods. Surfactants and other ingredients such as fluorophosphare including flavors can be included in the composition.

The Minute Fibril compositions that are effective for removing dental biofilm need to have sufficient strength such that when pressed over the tooth surface, with the aid or brush or applicator, it can interact and make contact with dental biofilm resulting in effective cleaning. The inventive network can comprise Minute Fibrils and abrading particles in sufficient amount so as to remove dental biofilm in a short time, for example in two minutes. The abrading particles can include silica, calcium carbonate at a concentration so that the particles can make contact with the tooth surface and assist in abrading and removing biofilm. The Minute Fibrils of the invention are cleared by the US Food and Drug Administration for use in food especially materials that are based on cellulose such as microfibrillated or nanofibrillated cellulose. The composition of the invention represent a new class of dentifrice which is different from current products that mainly depend on the action of abrasive particles.

Cleaning Contaminant Targets

Additional materials that can be cleaned with the compositions of the invention include without limitation biofilms, mineral deposits, sludge deposits (sewage or industria), pharmaceutical and cosmetics residues, environmental residues, food residues, skin debris and residues, makeup residues, wound debris, residues inside and outside body of host, automobile dirt and grime, bacteria disposed on a surface in healthcare setting, and the like. Additionally, the compositions of the invention can be used to increase the bonding receptivity of a surface for a new coat of paint or polymer. In embodiments, the surface is made ready for the new layer without providing visible scratch marks or cleaning sensitive surface such as automobiles and the like. Open Surfaces The cleaning open surfaces can be accomplished by application of manual or automated scrubbing or by other mechanical means including automated brushes or the like. The large surface area of the fibrillated structures makes them effective in removing contaminants from such open surfaces in distinction from already described flow inside channels. The inventive compositions can have yield shear stress from zero to several hundred Pascals as appropriate for the intended application. In embodiments, the compositions for open surfaces can usefully satisfy the condition of non-de-wetting on standing. The non-de-wetting property can be obtained by making compositions with some yield shear stress in order to prevent draining or de-wetting from the surface by gravity and/or by adjusting the formulation of the composition so that de-wetting can be avoided such as by adding an adhesion-promoting surfactant or polymer to the composition.

The effective cleaning of interior surfaces of endoscope channels with nano-fibers suspended in a fluid or gel is believed to be derived from the motion of said nano-fibers adjacent said interior surfaces. The efficiency of the cleaning process is believed to be increased by increasing the nano-fiber content of the cleaning formulation, and/or increasing the flow velocity of the cleaning formulation adjacent the surface being cleaned. Whereas, initially, increasing the flow velocity increases the cleaning efficiency, a point is reached wherein further increases in flow velocity is believed to result in a non-uniform dispersion of nano-fibers within the fluid, and a subsequent loss of some cleaning efficiency.

For enclosed channels, such as the lumen of a polymer tube in an endoscope, increasing the mass flow rate of the cleaning formulation through the lumen increases the flow velocity of the cleaning formulation adjacent the interior surface of the lumen. for open surfaces, other method are needed to cause the cleaning formulation adjacent to said open surfaces to flow with sufficient velocity parallel to said surface.

Figure 8:
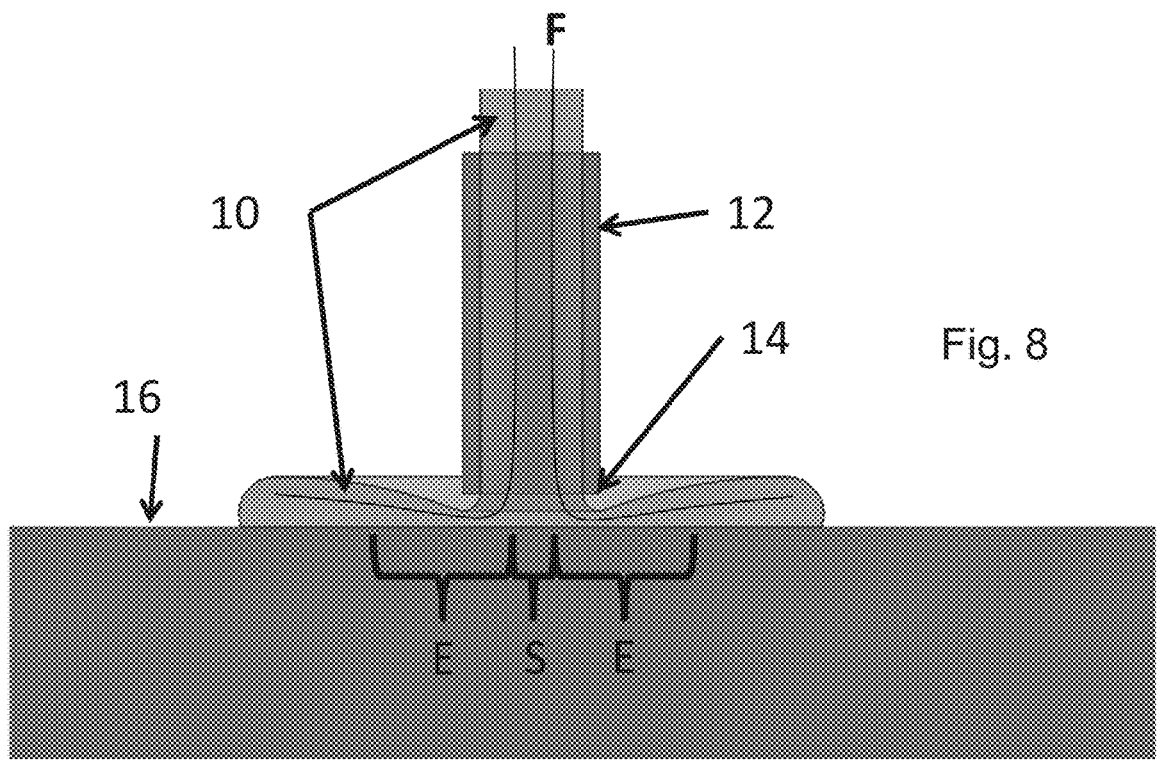
FIG. 8 shows an apparatus and method for cleaning an open surface.

A first device for (and method for) cleaning open surfaces is depicted in FIG. 8, wherein a cleaning formulation 10 is expelled through a delivery tube 12 and impinges upon an open surface 16, forming an ever expanding puddle surrounding delivery tube 12. Delivery tube 12 is positioned with tube end 14 close to, but not contacting open surface 16. Cleaning formulation 10 flows through delivery tube 12, and impinges upon open surface 16, proximal tube end 14, and then flows radially outward, as depicted by flow lines "F." A stagnation zone "S" is believed to exist at the center of the impingement area, wherein there is little to no fluid motion in the radial direction. Cleaning effectiveness in this zone may be low. Beyond zone "S", there exists an annular zone "E", wherein the radial velocity of cleaning formulation 10 is believed to be sufficient to produce efficient cleaning.

The radial velocity of cleaning formulation 10, exiting from tube end 14, is proportional to the mass flow rate of cleaning formulation 10 through delivery tube 12, and inversely proportional to the separation distance between tube end 14 and a given point on open surface 16. As the flow continues radially, the flow velocity decreases in proportion to the radius, and in proportion to the thickening of the outward flow, and cleaning becomes less efficient. To clean large areas, delivery tube 12 is moved laterally over open surface 16, such that all portions of open surface 16 are sufficiently cleaned.

Figure 1B:
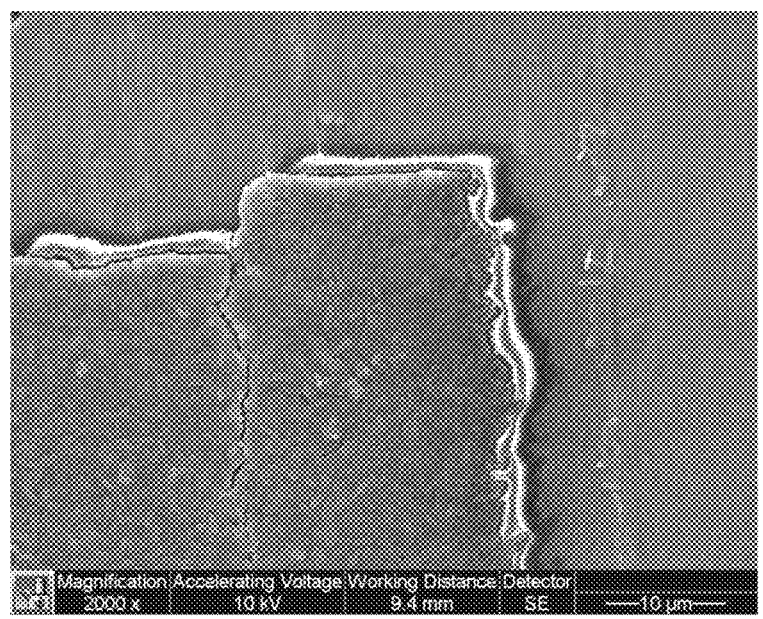
Figure 9:
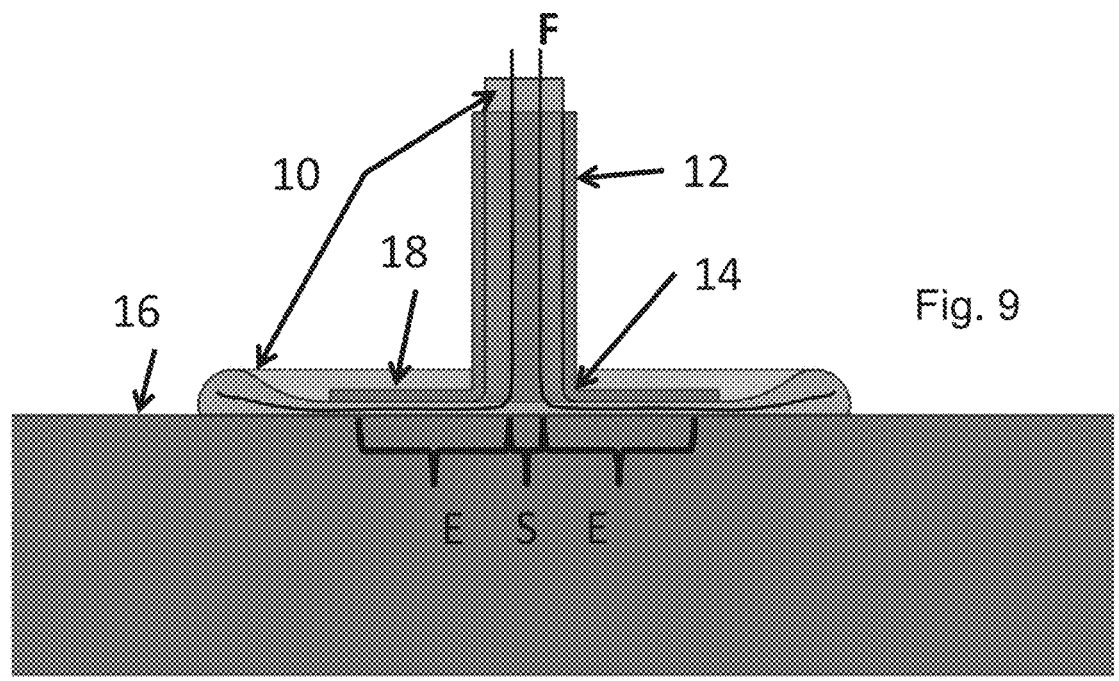
FIG. 9 shows another apparatus and method for cleaning an open surface.

In FIG. 9, a second embodiment of the apparatus of FIG. 1 comprises disk 18, appended radially to tube end 14. Delivery tube 12 is positioned with tube end 14 close to, but not contacting open surface 16. Disc 18 extends radially from tube end 14. Cleaning formulation 10 flows through delivery tube 12, and impinges upon open surface 16, proximal tube end 14, and then flows radially outward, between disc 18 and open surface 16, depicted by flow lines "F," to form an ever expanding puddle surrounding the perimeter of disc 18. In FIG. 4, the annular zone "E", wherein the radial velocity of cleaning formulation 10 is sufficient to produce efficient cleaning of open surface 16, is larger than the annular zone "E" of FIG. 2, as the presence of disc 18 prevents thickening of the of the outward flow in the area covered by disc 18, thus, a flow velocity sufficient for efficient cleaning of open surface 16 is maintained for a greater radial distance from delivery tube 12.

Apparatuses and Additional Methods for Cleaning an Open Surface

Figure 10:
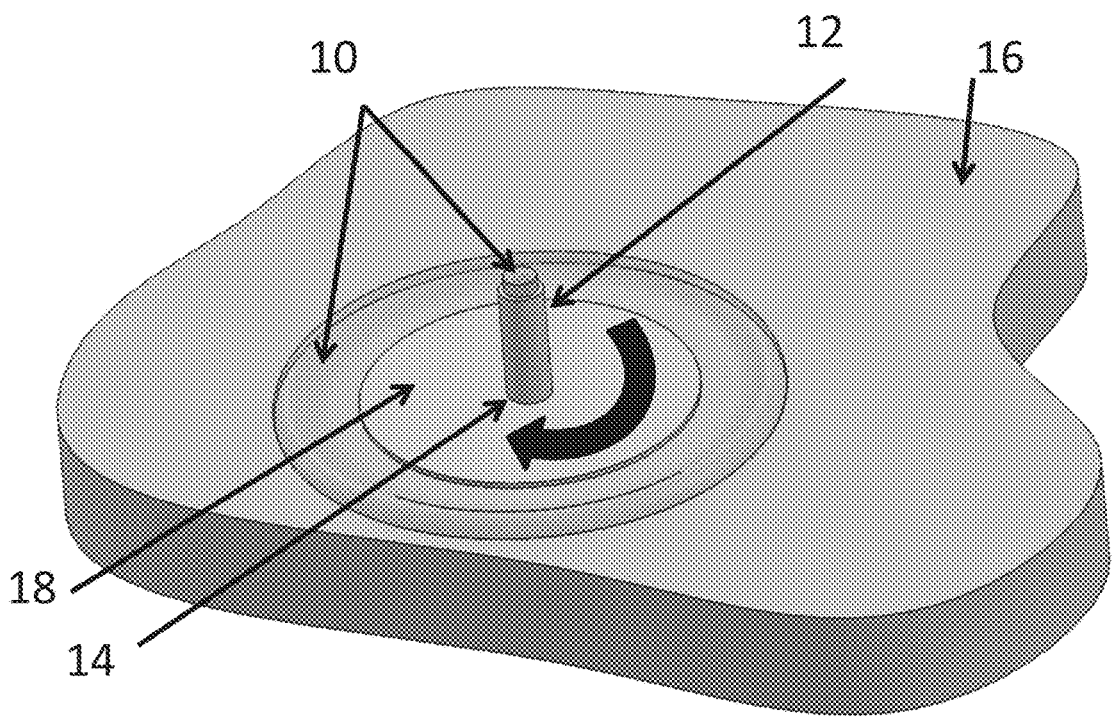
FIGS. 10 (oblique view), 11 (side view) and 12 (top, cut-away view) show another apparatus and method for cleaning an open surface.
Figure 11:
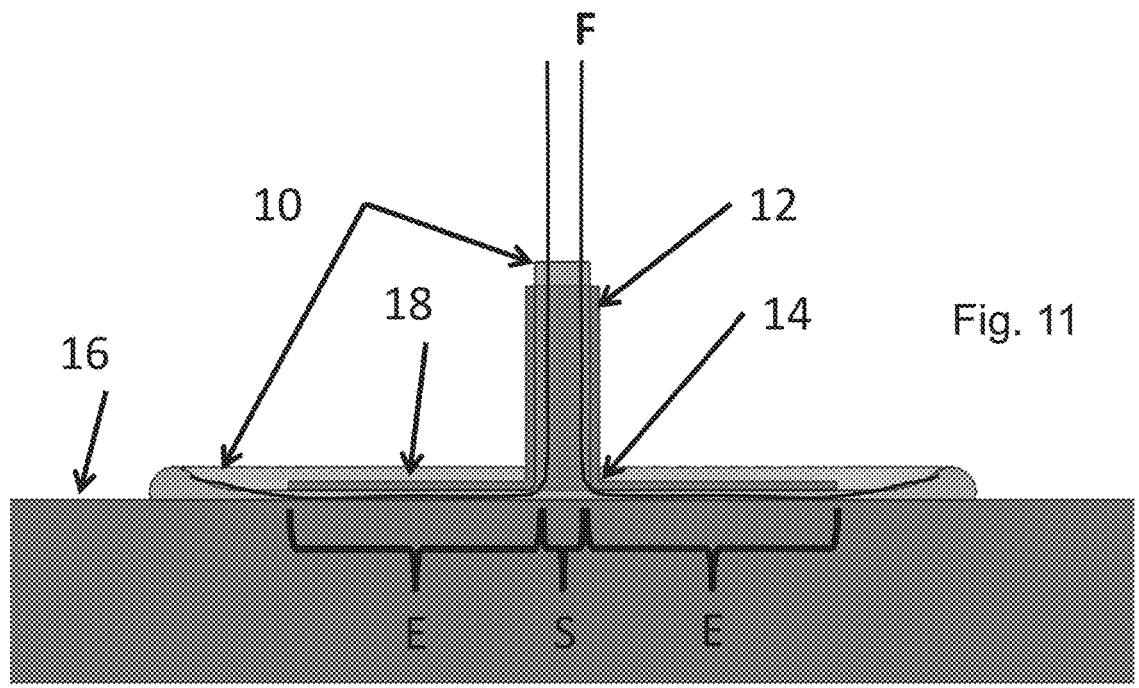

FIG. 10 shows the device of FIG. 9, wherein the disk 18 is rotated as indicated by the arrow. The science of fluid mechanics teaches that if a viscous fluid exists in a space between two parallel plates, and a first plate is held stationary, while the second plate is moved parallel to the first plate, a movement of the fluid layer, relative to the stationary plate is created by the viscous interaction between the fluid and the moving plate. This movement is proportional to the speed of the moving plate, and is called Couette flow. As shown in FIG. 11, the effect of this rotation is to expand the area "E" of more efficient cleaning.

Figure 12:
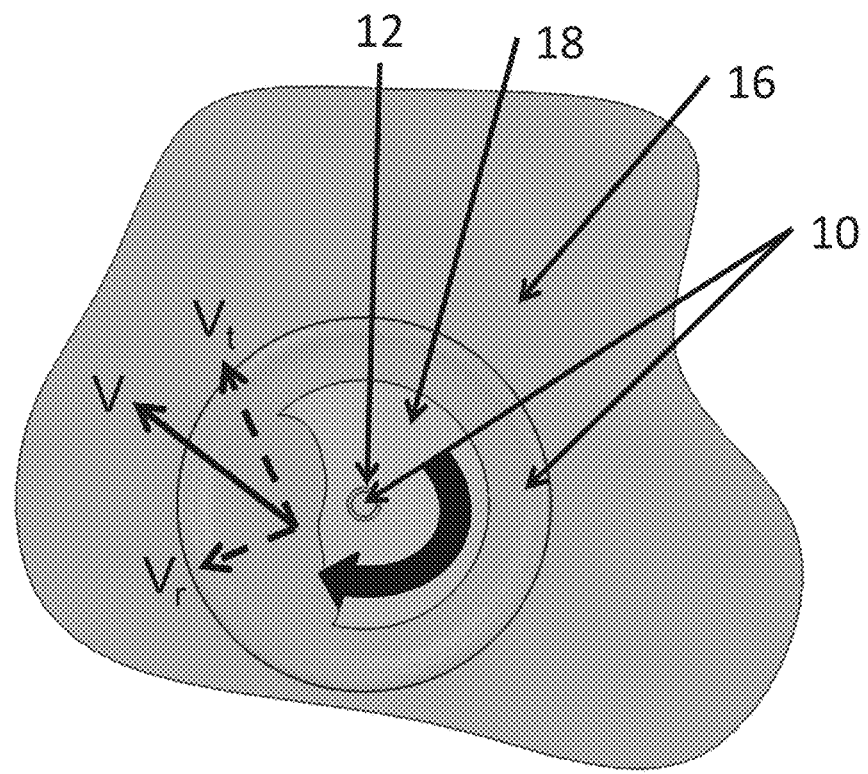

As shown in FIG. 12, (where a portion of disc 18 has been cut away, exposing a portion of underlying cleaning formulation 10) the motion of the fluid has a radial component "$V_r$," resulting from the flow of cleaning formulation 10 through delivery tube 12, and a tangential component "$V_t$" created by the Couette flow induced by the rotational motion of delivery tube 12, with appended disc 18. These two components add vectorially, to produce a flow velocity "V."

The radial component "$V_r$," is proportional to the mass flow rate of cleaning formulation 10 through delivery tube 12, and inversely proportional to the distance "R" from the center of delivery tube 12. The tangential component "$V_t$" is proportional to the tangential velocity of disc 18, which is calculated as the product of the angular rotational velocity of disc 18 and the radial distance "R" from the center of rotation.

Figure 13:
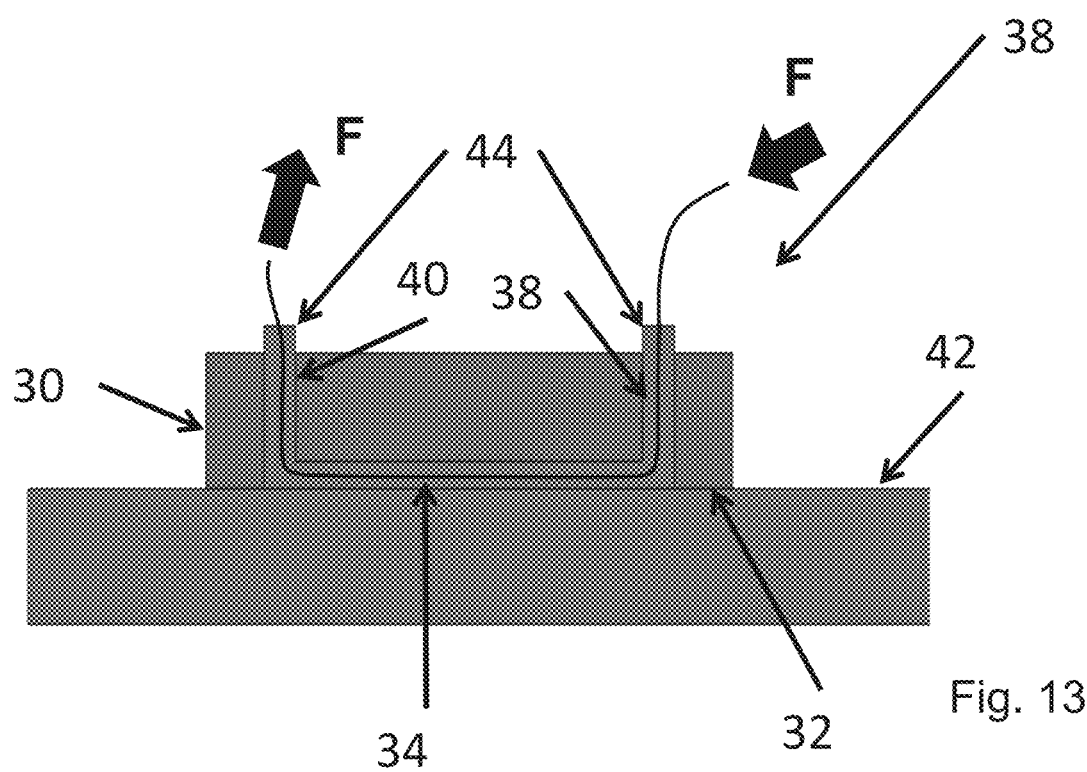
FIG. 13 show a further apparatus and method for cleaning an open surface.

Alternatively, large open surface areas can be cleaned by flowing a gel or fluid with suspended nano-fibers through channels formed between an open surface to be cleaned and a cleaning pad having a bottom surface held in contact with said open surface to be cleaned, said bottom surface having at least one open channel, said open surface to be cleaned forming closure of said at least one open channel. Referring to FIG. 13, cleaning pad 30 has a bottom surface 32, within which is formed an open channel 34. Cleaning pad 30 has a first port 38, which connects through cleaning pad 30 to an open channel 34, and a second port 40.

To clean a surface such as open surface 42, cleaning pad 30 is placed with bottom surface 32 of cleaning pad 30 in contact with open surface 42, as illustrated in FIG. 10, and a cleaning formulation 44 is injected into first port 38 of cleaning pad 30, and recovered from second port 40 of cleaning pad 30. When bottom surface 32 of cleaning pad 30 is placed in contact with open surface 42, open channel 34 in bottom surface 32 of cleaning pad 30, in conjunction with the portion of open surface 42 which spans open channel 34 in bottom surface 32 of cleaning pad 30, forms a closed conduit connecting first port 38 and second port 40.

Cleaning formulation 44, injected into first port 38, flows through the derived conduit, and is recovered from second port 40. The flow velocity of cleaning formulation 44 is chosen so as to produce maximum cleaning efficiency of that portion of open surface 42 spanning open channel 34 in bottom surface 32 of cleaning pad 30. Cleaning pad 30 is slowly moved over the entirety of open surface 42, to allow adequate time of flow of cleaning formulation 44 for every portion of open surface 42.

While not shown, one of skill will recognized that flow can be caused by a pump, which is any device suitable to cause a composition of the invention to flow. The devices of FIGS. 8-13 cause composition to flow into a confined space, such that a bulk shear stress can be defined.

Sterility

Those of skill will recognize when sterility of the composition is important. For example, in prep cleaning, sterility may be less important. Of course, antimicrobial agents or preservatives can be used to be sure that the compositions do not provide nutrients for further microbial growth. Sterilization of any component that is described anywhere herein can be performed by steam, gamma irradiation, Ethylene Oxide, electron beam, or any other known method of sterilization.

Additional Carrier Fluids

A possible carrier fluid is water, or an aqueous composition containing certain ingredients dissolved in it. However, the carrier fluid can be other materials including for example oily or oil-based liquids. The carrier fluid can comprise an organic solvent, possibly containing solutes dissolved in it. The carrier fluid can be an emulsion. Such emulsion could be an Oil-in-Water emulsion, or a Water-in-Oil emulsion, or a microemulsion. It is still further contemplated that the carrier fluid, in its condition prior to the mixing-in of the Minute Fibrils, can be a gel. The term carrier fluid is intended to encompass all of these possible fluids.

Other Surfaces to be Cleaned

The outside of the tubular portion of an endoscope tube can be cleaned for example by placing the tubular portion of an endoscope inside a larger tube, and causing a composition of an embodiment of the invention to flow through the annular region between the larger tube and the endoscope tube.

A medical device with which embodiments of the invention can be particularly useful is one having a channel configured to deliver or retrieve from the interior of an animal a fluid, a diagnostic device, an imaging device, or a surgical device. A diagnostic device can be, for example, endoscopes, ultrasound probes, optical devices of all kinds, or the like. An imaging device can be for example a fiber optic camera, a device that emits and receives electromagnetic or sound waves or the like. A surgical device can be for example a device that delivers a stent, a cutting tool, a clamping tool, a suturing tool or the like.

Devices for perfusing organs can be cleaned with the invention. CPAP devices (Continuous Positive Airway Pressure, a type of breathing therapy) can also be cleaned with the invention.

Another example of a device that can be usefully cleaned is an aspirating cannula, which can also be referred to as a suction/irrigation tube. Such devices can be used for a variety of medical, dental and other purposes. Such devices are often much more rigid than a typical endoscope. Such devices can be made of metal, or optionally a polymeric material that is sufficiently rigid. Also, in such devices the flowpath is often shorter, possibly even much shorter, than in a typical endoscope. Some such devices have one passageway. In some such cases, the passageway, especially if it is intended to be used for suction, can contain a vent hole. The vent hole can be covered by the finger of a user, or not covered, as desired. In use, a source of continuous suction can be connected to the proximal end of the device. The vent hole can be dimensioned such that if the vent hole is uncovered, the suction mainly is in communication with the atmosphere by way of the vent hole, and very little of the suction is felt at the distal tip of the device. If the vent hole is covered, the suction passageway is in communication with the distal tip of the device and can aspirate fluids from a site that is being treated. Sometimes the vent hole is elongated or teardrop-shaped so that it can be partially covered by the user's finger, as desired, to provide fine adjustment of the amount of suction delivered. Some such devices have two passageways, in which case one passageway can be used for delivering a fluid such as a liquid to the treatment site, and the other passageway can be used for suction or aspiration.

Such a device would have a path length L of the passageway, and would have an inside diameter D of the passageway. For such a device, the L/D ratio might be smaller than it is for a typical endoscope channel. Also, if such a device is made of metal or is more rigid than a typical endoscope, such a device can have passageway walls that are stronger and able to withstand a greater internal pressure. Taken together, for such a device, these facts can allow for the flowing of fluids that are more viscous than are permissible for typical endoscope channels, or can allow for flowing so as to create a larger shear stress at the walls.

In still other embodiments of the invention, in addition to cleaning channels of endoscopes, inventive compositions could be used for any of the following purposes: as a skin scrub, such as a surgical scrub to clean the surgical field before surgery; as a substance for cleaning sebaceous (oily) skin such as for acne; as a toothpaste (dentifrice) for removing biofilm, plaque, etc.; for cleaning the surface of a prosthesis, even a prosthesis that has already been implanted; As a debridement agent for wounds, including infected wounds; for cleaning membranes, such as for cleaning biofouling on membranes; and for removing mold (e.g., from building surfaces).

An example of a possible industrial (non-medical) application is cleaning the interiors of tubes of a heat exchanger. Such tubes are typically larger in inside diameter than the already-described endoscope channels, whose inside diameters are typically measured in millimeters. Heat exchanger tubes would typically have inside diameters that are measured in centimeters, and commonly they would be made of a metal. They could be cleaned by the described compositions and methods. The described compositions and methods can be used to clean any surface or pipe, such as cleaning radioactive deposits from pipes. They can be used in the form of a 'pig', i.e., as a discrete plug rather than a continuous flow of fluid, suitable to clean larger, as well as smaller, channels.

It would also be possible to use any of the described compositions or methods to clean wafers of semiconductor material, such as silicon, during the manufacturing of semiconductor wafers or circuits or products.

In applications in the cosmetics industry, when microfibrillated cellulose is used, it is typically used as a thickener (viscosity enhancer) in a formulation. The concentration of fibers is low compared to the concentration of surfactant, and the concentration of such fibers is typically in a range such that not much entanglement is created. Thus, if there is any cleaning effect from the fibrils it is small. The cosmetics industry prefers bacteria-originated fibrils, which are very fine, rather than fibrils that originate from wood pulp. For skin or mucosal uses, preferably the Minute Fibril concentration is from about 0.1% w/w to about 3% w/w.

Such cosmetic use can include use as a body wash, hand wash or shampoo, for use with any animal. In embodiments for cosmetic use, antimicrobial function is provided by appropriate essential oil(s).

The compositions of the invention can be used to clean or micro-sharpen blades.

Additionally, compositions of the invention can be used to clean the viewing screens of electronic devices, a surface of a precision cylinder, a cylinder-engaging surface of a piston, a food preparation surface, a surface of a gem, a glass surface.

Exemplary Minute Fibril Compositions

An exemplary base cleaning composition can comprise the materials defined as in Table 9:

TABLE 9

Water or solvent from about 95% to about 99% by weight
about 1 to about 5% Minute Fibrils or Minute Fibrils + gel-forming polymer
optional pH adjusting agent to provide a pH from about 2.0 to about 13.0
The mixture forming a fibrillated network The composition is sufficient to remove weakly adhering contaminants (it removes such contaminants, better than the vehicle alone), such as deposited organic soils and loose organisms mixed with the organic soil and young fragile biofilms. It may be less effective to remove mature or built-up crosslinked biofilms.

With one tested Minute Fibril composition at less than 0.5% in water, no fibrillated network formed, and the composition displayed minimal yield shear stress. When the concentration increased from about 0.5% to >2% by weight, a fibrillated network formed, which was evidenced by the composition having a yield shear stress of about 1.5 Pa at a fibrillated material concentration of 1% by weight, and a yield shear stress of about 40 Pa at a fibrillated material concentration of 1.4% by weight, as measured by storage modulus with the aid of a rheometer. Cleaning with a fibrillated network is preferred and cleaning with a network having yield shear stress of about 5 Pa to about 100 Pa (or about 5 Pa to about 60 Pa, or about 5 Pa to about 41 Pa) is also believed to be useful. Having an appropriate pH of the composition is helpful for removing contaminants Higher pH is believed to be more favorable for removing protein and organisms, and low pH is believed to be more favorable for removing inorganic deposits such as inorganic scale.

An exemplary base cleaning composition can be defined as comprising the components in Table 10:

TABLE 10

Water or solvent from about 95% to about 99% by weight
1 to 5% Minute Fibrils or Minute Fibrils + gel-forming polymer
Optional pH adjusting agent to provide pH from about 2.0 to about 13.0
Surfactant or surfactant mixture from about 0.01% to about 0.5% - surfactant can be nonionic, anionic, cationic, amphoteric or mixture thereof)
Optionally the mixture forming a fibrillated network An exemplary base cleaning composition can be defined as comprising the components in Table 11:

TABLE 11

Water or solvent from about 95% to about 99% by weight
1 to 5% Minute Fibrils or Minute Fibrils + gel-forming polymer
Optional pH adjusting agent to provide pH from about 2.0 to about 13.0
Surfactant or surfactant mixture from about 0.01% to about 0.5% - surfactant can be nonionic, anionic, cationic, amphoteric or mixture thereof)
Optionally the mixture forming a fibrillated network
Stiffening or Abrasive Components (e.g., about 0.1% to about 5% by weight of the composition, or about 0.1% to about 3% by weight An exemplary base cleaning composition can comprise materials defined as in Table 12:

TABLE 12

Water and organic solvent from about 95% to about 99% by weight, water comprising a major portion of the solvent component
1 to 5% Minute Fibrils or Minute Fibrils + gel-forming polymer
Optional pH adjusting agent to provide pH from about 2.0 to about 13.0
Surfactant or surfactant mixture from about 0.01% to about 0.5% -

TABLE 12-continued surfactant can be nonionic, anionic, cationic, amphoteric or mixture thereof)
The mixture forming a fibrillated network All such compositions can comprise additional components described herein, including antimicrobials, antibiotics, surfactants, and the like.

Exemplary Effective Cleaning Conditions

Below in Tables 13, 14 and 15 are conditions that proved successful in removing BBF from narrow channels. The carrier fluid was substantially similar to CS-19, with the pH from about 10 to about 11.

TABLE 13

| # | Int. Dia mm | Length cm | Feed Composition Main Component Desc. | wt % | Additive Desc. | wt % |
|---|---|---|---|---|---|---|
| 1 | 1 | 10.16 | 3:1 Epl/Ef | 1 | None | 0.0 |
| 2 | 1:37 | 10.16 | 3:1 Epl/Ef | 1.2 | NT200 | 2.0 |
| 3 | 1.6 | 10.16 | 3:1 Epl/Ef | 1.2 | NT200 | 1.0 |
| 4 | 3.2 | 91.44 | 3:1 Epl/Ef | 1.7 | None | 0.0 |
| 5 | 3.7 | 10.16 | 3:1 Epl/Ef | 1.9 | NT200 | 2.0 |

TABLE 14

| | Feed Composition | | | | Rinse Data | | |
|---|---|---|---|---|---|---|---|
| # | Weight to clean g | Clean time min | Target Δ Press. psi/ft | Actual Flow Rate g/min | Rinse time min | Rinse rate mL/min | Reynolds No. Re |
| 1 | 19 | 8 | 1.9 | 2.4 | 1 | 60 | 1,273 |
| 2 | 16 | 8 | 2.7 | 2.0 | 5 | 100 | 1,549 |
| 3 | 85 | 8 | 1.9 | 10.6 | 1 | 140 | 1,857 |
| 4 | 110 | 4 | 1.9 | 27.5 | 3 | 333 | 2,211 |
| 5 | 140 | 8 | 1.8 | 17.5 | 3 | 333 | 1,912 |

TABLE 15

| | Feed Composition Data | | | | |
|---|---|---|---|---|---|
| # | Linear Velocity cm/sec | Apparent Viscosity mPa-sec | Apparent Reynolds No. Re | Shear stress at wall, Pa | Shear Rate 1/sec |
| 1 | 5.0 | 2,774 | 0.02 | 10.7 | 403 |
| 2 | 2.3 | 4,682 | 0.01 | 20.8 | 132 |
| 3 | 8.8 | 620 | 0.23 | 17.1 | 441 |
| 4 | 5.7 | 240 | 0.76 | 34.2 | 143 |
| 5 | 2.7 | 357 | 0.28 | 37.4 | 59 |

Protocol for Oil Burden Testing

For Oil burden testing, a 6 foot section of Teflon® tubing with 3.2 mm ID is used. The entire tubing is filled with JIF creamy peanut butter. According to its label, this peanut butter is made from roasted peanuts and sugar, and contains 2% or less of: molasses, fully hydrogenated vegetable oils (rapeseed and soybean), mono and diglycerides, salt. Also, according to its label, a 32 g serving contains: 190 calories, 16 g fat (sat. fat 2.5 g, trans fat 0 g, chol. 0 mg), carbohydrate 8 g (dietary fiber 2 g, sugars 3 g), protein 7 g. Cleaning efficiency is viewed visually. A positive result is considered to be tubing that is visually indistinguishable from the negative control (tubing without any peanut butter). In embodiments, compositions of the invention remove oil burden by this test.

BBF Cleaning in a Channel

To test removal of BBF as manufactured as described herein, the middle of the channel (tubing) is cut open lengthwise and is examined by a Scanning Electron Microscope and culturing. Where the positive control shows a clear biofilm, a positive biofilm removal is shown by the two test samples being free of the biofilm (substantially equal to the negative control). In embodiments, the compositions of the invention are successful in removing BBF.

BBF Cleaning from an Outer Surface

On open surfaces cleaning is examined by a Scanning Electron Microscope. Where the positive control shows a clear biofilm, a positive biofilm removal is shown by the two test samples being free of the biofilm (substantially equal to the negative control). In embodiments, the compositions of the invention are successful in removing BBF.

Bioburden Testing

For bioburden testing, a 6 foot section of Teflon® tubing with 3.2 mm Inside Diameter is used. The entire tubing is filled with the Austrian Soil (iso.org; ISO/TS 15883-5:2005 (E)) containing ~10^8 CFU/mL of each of *Enterococcous faecalis, Pseudomonas aeruginosa,* and *Candida albicans*. The soil is left in the tubing for 2 hours.

The harvesting method for the channel is performed according to the flush-brush-flush method [Alfa et al., 2016, BMC Res Notes 9: 258; Alfa et al., 2016, J Hosp Infect 93: 83-88]. The collected sample is 40 mL sterile reverse osmosis (sRO) water and includes the tip of a cleaning brush.

Collected samples are processed by the following sequence: 1 minute vortex, 3 times of 5 second sonication, and 1 minute vortex. Protein quantitation is performed using the QuantiPro™ BCA Assay Kit. Bovine serum albumin is used as the protein standard (Sigma-Aldrich, St. Louis, Mo.). Hemoglobin is measured using the 3,3',5,5'-tetramethylbenzadine liquid substrate system for enzyme-linked immunosorbent assay (Sigma-Aldrich, St. Louis, Mo.) with 80 mg/dL cyanmethemoglobin standard (Stanbio Laboratory, Boerne, Tex.). Carbohydrates are measured by the phenol-sulfuric acid with a glucose standard method. Bioburden quantitation is performed using serial dilutions of 1:10 followed by the spread plate method using 0.1 mL of each dilution onto BBL CHROMagar™ Orientation Media (Becton Dickinson, Franklin Lakes, N.J.).

A positive result is defined by: a reduction of about 99.5% or greater in protein, a reduction of about 99.5% or greater in carbohydrate, and a Reduction Factor RF for the reduction in each of the three bacteria of about 6.0 or higher, meaning 6 orders of magnitude. In preferred embodiments, compositions of the invention are effective in yielding a positive result regarding bioburden removal.

Specific embodiments according to the methods of the present invention will now be described in the following examples. The examples are illustrative only, and are not intended to limit the remainder of the disclosure in any way.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

Where a sentence states that its subject is found in embodiments, or in certain embodiments, or in the like, it is applicable to any embodiment in which the subject matter can be logically applied.

Example 1

This example describes a protocol for preparing biofilm for use in the described experiments. This protocol produces what can be called traditional biofilm ("TBF").

Preliminary Steps

1. Subculture *Enterococcus faecalis* ATCC 29212 and *Pseudomonas aeruginosa* ATCC 15442 on blood agar (BA) plates. The organisms should be 24 hours old on the day of experiment.

2. Sterilize the 6-foot lengths of 3.2 mm ID PTFE tubing required for testing, in the Steris System IE (include BI and CI). Dry thoroughly. Be sure the required lengths are sterilized no more than 7 days prior to testing.

3. Prepare ATS-2015 with 20% defibrinated sheep blood (this soil can be stored up to 2 weeks in the refrigerator). The organisms will be suspended in Artificial Testing Soil (ATS) as published by Alfa et al. (Ref "Alfa et al., 2010. EVO-TECH® endoscope cleaner and reprocessor (ECR) simulated-use and clinical-use evaluation of cleaning efficacy, BMC Infectious Diseases. BMC Infectious Diseases 2010, 10:20 www.biomedcentral.com/1471-2334/10/200)"). The ATS soil was developed to mimic organic residues left in flexible endoscopes after a gastro-intestinal endoscopic procedure, including protein, carbohydrate and hemoglobin.

EXPERIMENTAL

1. On Sunday night, make appropriate soil/bug suspension (EF and PA each at ~108 cfu/mL in ATS-2015 containing 20% sheep blood) and perform an inoculum count. Feed this suspension through the appropriate length of PTFE tubing (pre-sterilized in the Steris System 1E) while attached to a pump. Circulate the soil at pump setting 5.8 overnight (~1.2 ml/min)—but in any case adjust the flow rate so as to maintain continuous uninterrupted circulation.

2. On Monday morning, make appropriate soil/bug suspension (EF and PA each at ~105 cfu/mL in 1:10 diluted ATS-2015 containing 20% sheep blood) and perform an inoculum count. Turn pump off and expel the soil from the PTFE length while still attached to the peristaltic pump tubing and return soil to the original container. While still attached to the pump tubing, push through (slowly) 20 mL of sRO water+30 mL of air using a 60 cc luer lock syringe. Detach PTFE from the pump (clean the pump tubing) and bring the PTFE under the biological safety cabinet ("BSC") inside a container. Push 30 mL of sRO water+30 mL of air through the PTFE into a discard container. Repeat×2. Push some air through to dry the tubing. Re-soil (EF and PA each at ~105 cfu/mL in 1:10 diluted ATS-2015 containing 20% sheep blood) and attach to the pump (using new pump tubing) and circulate at pump setting 5.8 until the following morning.

3. On Tuesday through Thursday, repeat rinsing/soiling of tubing exactly as per Monday. Soil overnight using the 105 cfu/mL soil/bug suspension until Friday morning.

4. On Friday (Day 5), rinse with sRO water exactly as per previous days. Dry and perform destructive and other testing as required.

Example 2

To make BBF, the bacteria, ATS and tubing material described above are used in the following protocol:

| Day of week | GROWTH STEP ATS-Bacteria Inoculation: (time of | Rinse Sterile Tap Water Rinse (20 mL | Glutaraldehyde Glutaraldehyde Exposure (1:50 dilution; | Rinse Sterile Tap Water Rinse (30 mL | |
|---|---|---|---|---|---|
| DAY | Day of Week: | circulation using pump) | water + 30 mL air) | 0.05%, 2 minutes) | water + 30 mL air × 3) | END OF DAY instruction: |
| 1 | Mon | Growth Step: ATS-bacteria circulates (pump setting 5.8, ~1.2 ml/min) | | | | |
| 2 | Tues | Growth Step: ATS-bacteria circulates (pump setting 5.8, ~1.2 ml/min) | | | | |
| 3 | Wed | Growth Step ends at 48 h | ✓ | ✓ | ✓ | Fill Tubing with sterile water (O/N at RT) |
| 4 | Thurs | ✓ (4 hours) | ✓ | ✓ | ✓ | Fill Tubing with sterile water (O/N at RT) |
| 5 | Fri | ✓ (4 hours) | ✓ | ✓ | ✓ | Begin Growth Step |
| 6 | Sat | Growth Step: ATS-bacteria circulates (pump setting 5.8, ~1.2 ml/min) | | | | |
| 7 | Sun | Growth Step: ATS-bacteria circulates (pump setting 5.8, ~1.2 ml/min) | | | | |
| 8 | Mon | Growth Step ends | ✓ | ✓ (FULL STRENGTH 2.6% GLUT for 20 MIN) | ✓ | Flush some air thru channel to remove excess fluid. |

Example 3

Rinsing Minute Fibrils

A rinsing experiment was performed in the air and water channels of an Olympus Colonoscope (Model No. CF-100L). A gel containing Exilva Forte at a concentration of 2% (by weight) in CS-19 was recirculated in the air and water channels of this endoscope for 10 hours using a metering pump (Model No. PM60, Fluid Metering, Inc., Syosset, N.Y.). The gel was injected through the air-water port and air channel at the umbilical end of this endoscope, and it flowed all the way to the distal end of the endoscope. The flow rate of this gel inside the colonoscope was 8.5 mL/min and the average pressure measured at the inlet of the colonoscope was about 24 psi. The colonoscope was then rinsed with water prepared by Reverse Osmosis (RO) at a flow rate of 200 ml/min for 10 minutes using the same metering pump. The rinsing water was also injected through the air-water port and through the air pipe at the umbilical end simultaneously. The average pressure at the inlet of the colonoscope during rinsing was about 14 psi. After the completion of both the cleaning and the rinsing, a sampling procedure was performed on this colonoscope using a two-phase flow recovery method using 0.075% Tween-20 solution and HEPA-filtered air at 28 psi set pressure. The flow rate of Tween-20 solution during two-phase flow was 16 ml/min and the air pressure dropped to about 20 psi during two-phase flow. A total volume of about 200 ml of Tween-20 solution was used during this experiment using two-phase flow to check the quality of rinsing. The outflow was collected as four separate samples, which are described as follows.

Sample 1: This sample (about 40-50 ml) was collected in a transparent cup after 3 minutes of two-phase flow. We observed some long fibers and coagulation of fibers in this sample. Also, one drop (~0.2 gm) of this sample was put on a microscope slide and one long fiber was observed under the microscope. Sample 2: This sample (about 40-50 ml) was collected in a transparent cup from the 3 minute time point to the 6 minute time point of two-phase flow. We observed some long fibers but fewer than with Sample 1. Sample 3: This sample (about 40-50 ml) was collected in a transparent cup from the 6 minute time point to the 9 minute time point of two-phase flow. We observed approximately the same number of fibers as with Sample 2. Sample 4: This sample (about 40-50 ml) was collected in a transparent cup from the 9 minute time point to the 12 minute time point of two-phase flow. We observed some fibers in this sample but fewer than with Samples 2 and 3. Accordingly, the Minute Fibrils can be removed under practical conditions.

In a related experiment, Applicant noted that Minute Fibrils can be trapped in the air-water cylinder (spool valve region) in the handle area, such that this area and like complex structures should be carefully rinsed.

Example 4—Minute Fibril Flow Through 1.6 mm Channel

Exilva Forte—1%

A gel containing 1% Exilva Forte (Borregaard) gel in CS-19 was recirculated in the air and water channels of an Olympus Colonoscope (Model No. CF-100L) for a total of 22 hours using a metering pump (Model No. PM60, Fluid Metering, Inc., Syosset, N.Y.) as follows: The gel was injected through the air-water port at the umbilical end of this colonoscope and recirculated for a total of 10 hours. Then the gel was injected through the air-water port and air pipe at the umbilical end of this colonoscope and was recirculated for 6 hours. Then, the gel was injected through the air pipe at the umbilical end of this colonoscope (with the air-water port at the umbilical end being closed) and was recirculated for 6 hours.

The flow rate of gel inside the colonoscope was 8.5 ml/min and the average pressure measured at the inlet of the colonoscope was about 24 psi. After each step, the colonoscope was rinsed with Reverse Osmosis water at a flow rate of 200-250 ml/min for 10-15 minutes. The rinsing water was also injected through the same port(s) as the gel and the average pressure at the inlet of the colonoscope during rinsing was about 14 psi.

No clogging was observed. This example shows that gel containing Exilva Forte at a 1% concentration can pass through the small (air and water) channels of an endoscope without clogging.

Exilva Forte—2%

A gel containing Exilva Forte at a concentration of 2% (by weight) in CS-19 was recirculated in the air and water channels of an Olympus Colonoscope (Model No. CF-100L) for a total of 10 hours using a metering pump (Model No. PM60, Fluid Metering, Inc., Syosset, N.Y.) as follows: The gel was injected through the air-water port and air pipe at the umbilical end of this colonoscope and recirculated for a total of 10 hours.

The gel flow rate inside the colonoscope was 8.5 ml/min and the average pressure measured at the inlet of the colonoscope was about 24 psi. After each step, the colonoscope was rinsed with Reverse Osmosis water at a flow rate of 200 ml/min for 15 minutes. The rinsing water was also injected through the air-water port and the air pipe at the umbilical end of the endoscope, and the average pressure at the inlet of the colonoscope during rinsing was about 14 psi.

No clogging was observed. This example shows that gel containing Exilva Forte at a somewhat higher concentration than in the previous example, i.e., a 2% concentration, can also pass through the small (air and water) channels of an endoscope without clogging.

It can be noted that concentrations such as are reported here are calculated as the dry weight of the Exilva product, compared to the total weight of the composition. It can be noted that the Exilva product is usually shipped wet, but for purposes of characterizing concentration of Minute Fibrils in a composition, reference is made to weight of the fibrils when they are dry.

Example 5—Cleaning Bioburden

In soiling experiments described herein, unless indicated otherwise, soiling was made with Austrian Soil. Following are the volumes of soil used to contaminate the channels: 10 mL for 3.2 mm ID tube and 3 mL for 1.6 mm ID tube. The soil was left to stand in tube for 2 hrs, followed by cleaning and rinsing followed by harvesting of remaining contaminants. Harvesting was done using Sterile Reverse Osmosis water and other protocols as described elsewhere.

ATS soil as developed by Alfa (U.S. Pat. No. 6,447,990) was used as a surrogate to indicate medical device cleaning by measuring remaining protein, carbohydrate and hemoglobin in the tube or channel after cleaning as per the protocol described elsewhere herein. Other organic soils simulants were also used to demonstrate embodiment of the invention. The "Austrian Soil" was made according to ISO standard ISO/TS 15883-5: 2005.

The Minute Fibril composition used in this example was 0.4% Nanofibrillated cellulose made by EFT company at a concentration of 0.4%. The concentration is by weight, and refers to dry weight of the fibers in conjunction with weight of the carrier fluid. The gel was made in the CS-19 carrier fluid. The composition was made by homogenizing the fibrillated material in the CS-19 carrier fluid for 5 minutes or until a homogeneous gel network was formed. The cleaning network composition was stable during storing without separation. All cleaning experiments were performed at room temperature unless otherwise indicated. Rinsing was done with distilled water. The details of experiments are given in the following tables.

TABLE

Test Conditions for 3.2 mm inside diameter of channel:

|  | Duration (min) | Flow rate (ml/min) | Pressure drop (psi) | Temperature (° C.) |
|---|---|---|---|---|
| Cleaning | 3 | 280 | 0 | RT |
| Rinsing | 3 | 560 | 0 | RT |

TABLE

Test Conditions for 1.6 mm inside diameter of channel:

|  | Duration (min) | Flow rate (ml/min) | Pressure drop (psi) | Temperature (° C.) |
|---|---|---|---|---|
| Cleaning | 3 | 140 | <10 | RT |
| Rinsing | 3 | 280 | <15 | RT |

TABLE

Organic Soil Results:

|  | Channel ID = 3.2 mm, Length = 183 cm | | Channel ID = 1.6 mm, Length = 183 cm | |
|---|---|---|---|---|
|  | Conc. (µg/ml) | Conc. (µg/cm$^2$) | Conc. (µg/ml) | Conc. (µg/cm$^2$) |
| Protein (Benchmark is <6.4 µg/cm$^2$) | | | | |
| PC | 4348 | 1123 | 3261 | 815 |
| NC | 0.761 | 0.166 | 0.652 | 0.142 |
| Cleaning Test 1 | 1.087 | 0.236 | 0.109 | 0.024 |
| Cleaning Test 2 | 0.652 | 0.149 | 0.217 | 0.047 |
| Carbohydrate (Benchmark is <1.8 µg/cm$^2$) | | | | |
| PC | 17500 | 4521 | 17917 | 4483 |
| NC | 5.833 | 1.269 | 6.667 | 1.451 |
| Cleaning Test 1 | 1.25 | 0.272 | 3.333 | 0.761 |
| Cleaning Test 2 | 0 | 0 | 7.5 | 1.632 |

PC is positive control, soiled no cleaning; NC is negative control, is brand new tube without soil; Cleaning Test 1 and Cleaning Test 2 are duplicates of each other.

The values of 6.4 micrograms protein and 1.8 micrograms carbohydrate are benchmarks of what is considered acceptable cleaning according to industry as originally published by Alfa et al. For a device to be considered clean, the measured value for carbohydrate after cleaning must be less than the benchmark value of 1.8 microgram/cm^2. Cleaning with the inventive technology achieved cleaning levels that certainly way below this benchmark value.

The results of this example show that the measured residual protein levels after cleaning soiled tubes are almost the same as the negative control. This indicated that almost all organic soil is removed from the channels. In fact, results are achieved that are even cleaner than the negative control, which means that this technology removed contaminants that were present from manufacturing.

The experiment was repeated with soiling was done with Austrian Soil and the tubing was allowed to sit in a wet condition for 30 min followed by flowing air through the tubing for 1 hr 30 min to dry out the soil, followed by cleaning. Even the soil was allowed to dry in the channel, the results were substantially the same.

Example 6—Cleaning Bioburden

This example shows the removal of ATS soil (Artificial Test Soil-T) (U.S. Pat. No. 6,447,990). This is a repeat of Example 4 with the only difference being that the organic soil was a different soil from the soil that was used in Example 4. Cleaning and rinsing conditions were identical to those used in Example 4.

|  | Channel ID = 3.2 mm, Length = 183 cm | | Channel ID = 1.6 mm, Length = 183 cm | |
|---|---|---|---|---|
|  | Conc. (µg/ml) | Conc. (µg/cm$^2$) | Conc. (µg/ml) | Conc. (µg/cm$^2$) |
| Protein (Benchmark is <6.4 µg/cm$^2$) | | | | |
| PC (10$^{-2}$) | 31.141 (3114.1) | 7.283 (728.3) | 26.913 (2691.3) | 6.441 (644.1) |
| NC | 0 | 0 | 0 | 0 |
| Cleaning Test 1 | 0 | 0 | 0.201 | 0.044 |
| Cleaning Test 2 | 0 | 0 | 0 | 0 |
| Carbohydrate (Benchmark is <1.8 µg/cm$^2$) | | | | |
| PC (10$^{-2}$) | 0 | 0 | 8.8 (880) | 2.106 (210.6) |
| NC | 0 | 0 | 0 | 0 |
| Cleaning Test 1 | 0 | 0 | 0 | 0 |
| Cleaning Test 2 | 0 | 0 | 0 | 0 |
| Hemoglobin (Benchmark is <2.2 µg/cm$^2$) | | | | |
| PC (10$^{-2}$) | 3.089 (308.9) | 0.722 (72.2) | 1.951 (195.1) | 0.467 (46.7) |
| NC | 0 | 0 | 0 | 0 |
| Cleaning Test 1 | 0 | 0 | 0 | 0 |
| Cleaning Test 2 | 0 | 0 | 0 | 0 |

Similar experiments were conducted where *Enterococcus faecalis* (EF), *Pseudomonas aeruginosa* (PA) and *Candida albicans* (CA) were introduced into the soil. In those experiments, zero colony forming units were recovered after cleaning, even for narrow 1.6 mm channels. These results demonstrate that remarkable cleaning levels can be achieved even without traditional mechanical brushing.

Example 7—Cleaning Bacteria—Laden Bioburden with Minute Fibrils Only

Substantially the bioburden testing with added *Enterococcus faecalis* (EF), *Pseudomonas aeruginosa* (PA) and *Candida albicans* (CA) was repeated. However the cleaning composition was: 0.4% NFC (EFTec™ Nanofibrillated Lyocell Fiber Type L040-6SEFT (cellulose fibers)) in RO water. This uses Minute Fibril structure in pure water without any other additives, including without surfactant. The results met cleaning specifications for bioburden. For bacteria, the worst result was for *Pseudomonas aeruginosa* in a 3.2 mm channel, with the result being 3.00×10 (vs. positive control of 1.78×10^8). This example shows that the mechanical action of the Minute Fibrils alone is sufficient to clean this bioburden and organic soil. In other experiments, the inclusion of other ingredients in the network composition further improves cleaning and decreases the cleaning times as well.

Example 8—Cleaning Biofilm

Figure 5A:
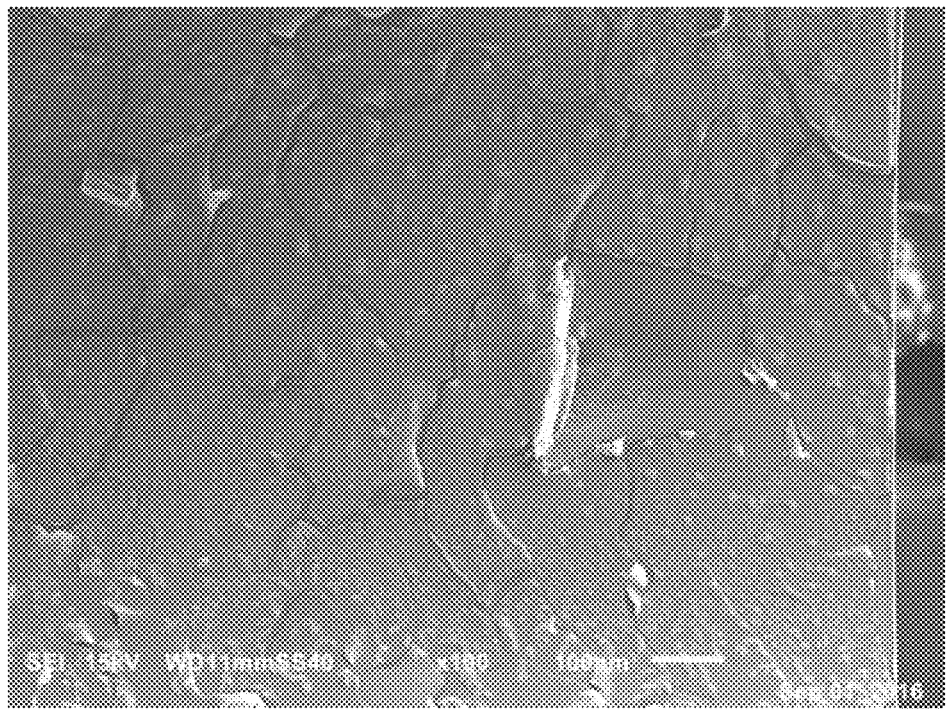
FIG. 5A (see 100 micron bar) shows biofilm in a channel by SEM.
Figure 5B:
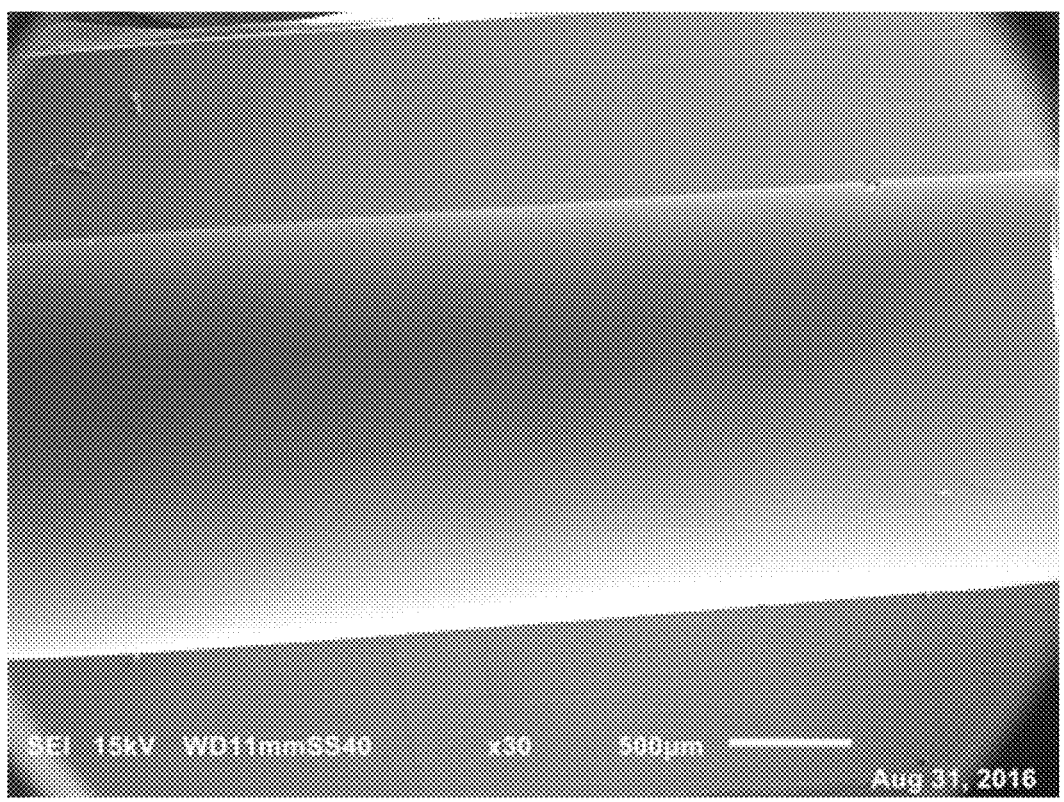
FIG. 5B (see 500 micron bar) shows biofilm removal in a channel with Minute Fibrils.
Figure 5C:
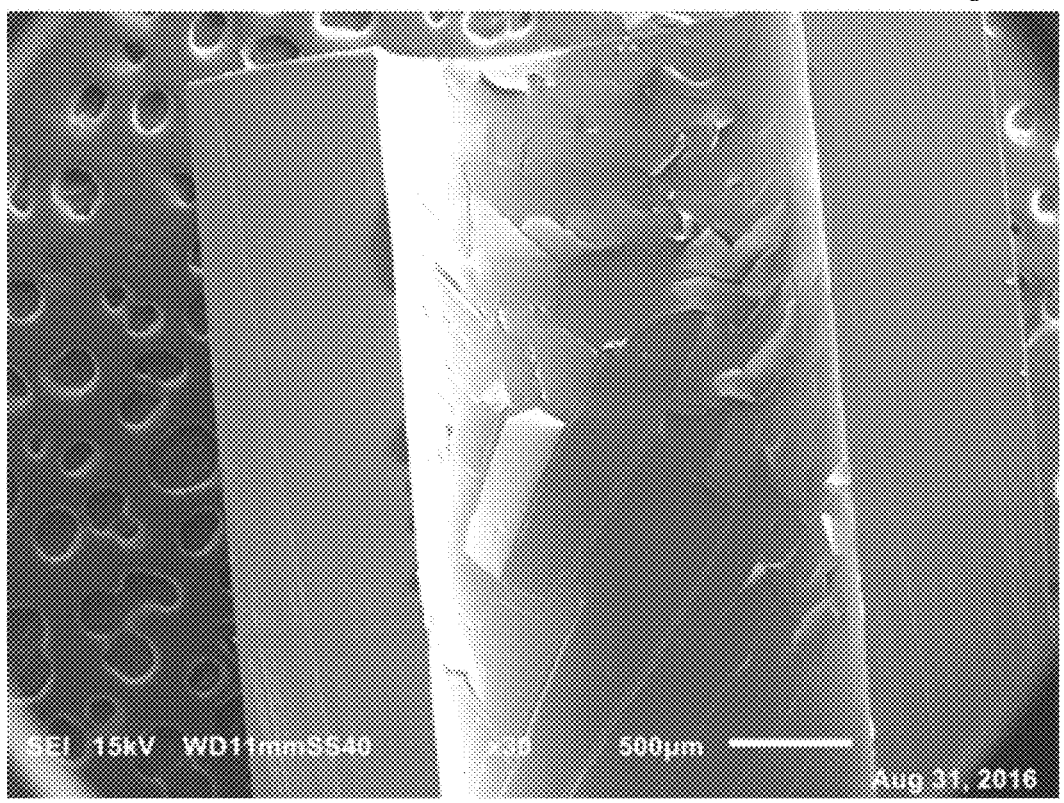
FIG. 5C (see 500 micron bar) shows incomplete biofilm removal with conventional cleaning.
Figure 6A:
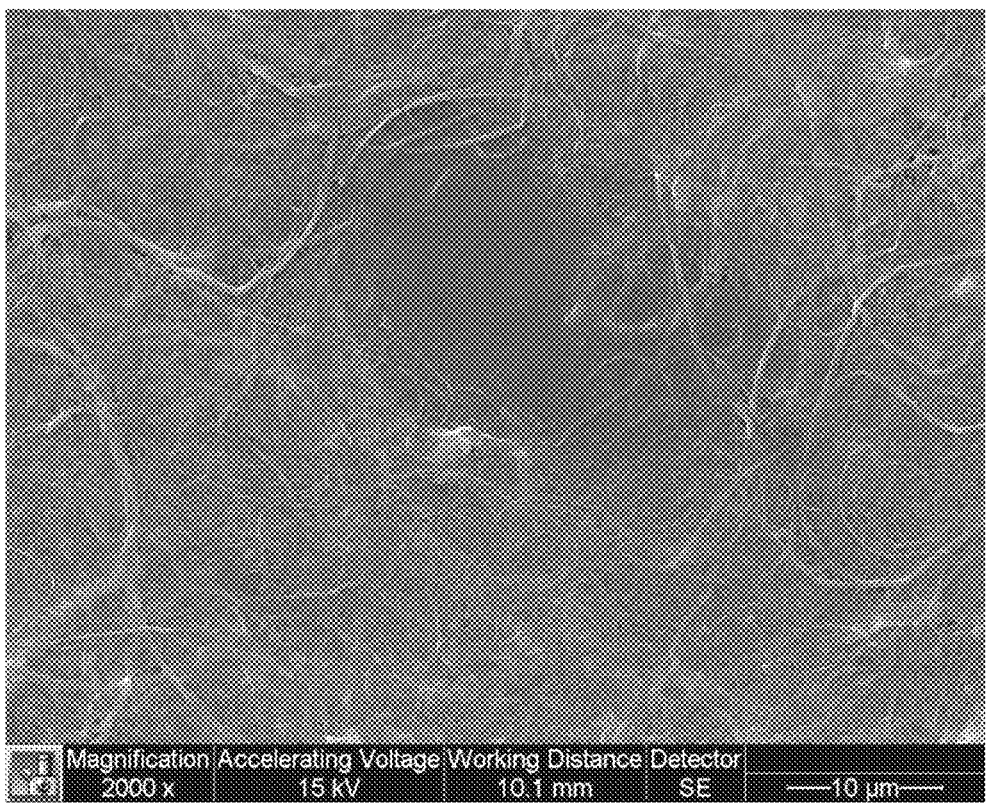
FIGS. 6A (see 10 micron bar) and 6B (see 500 micron bar) show an exemplary structure of a Minute Fibril composition as visualized by SEM, specifically 1.4% w/w Exilva Forte in Modified CS19 (carrier fluid described below)
Figure 6B:
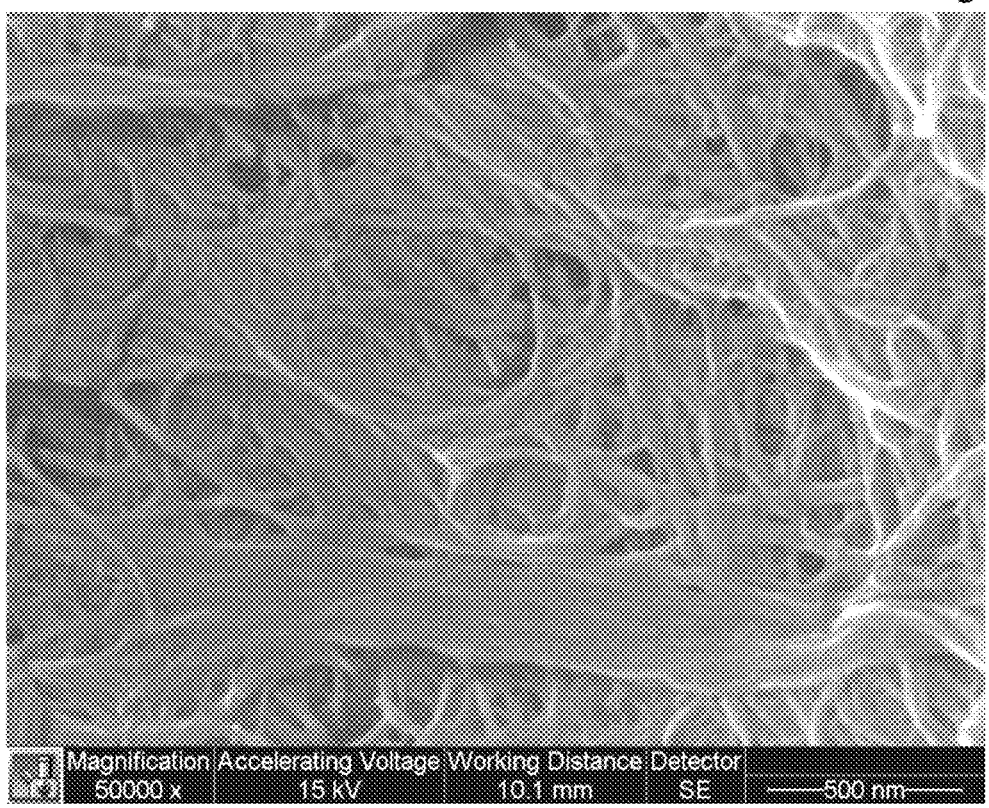
Figure 7:
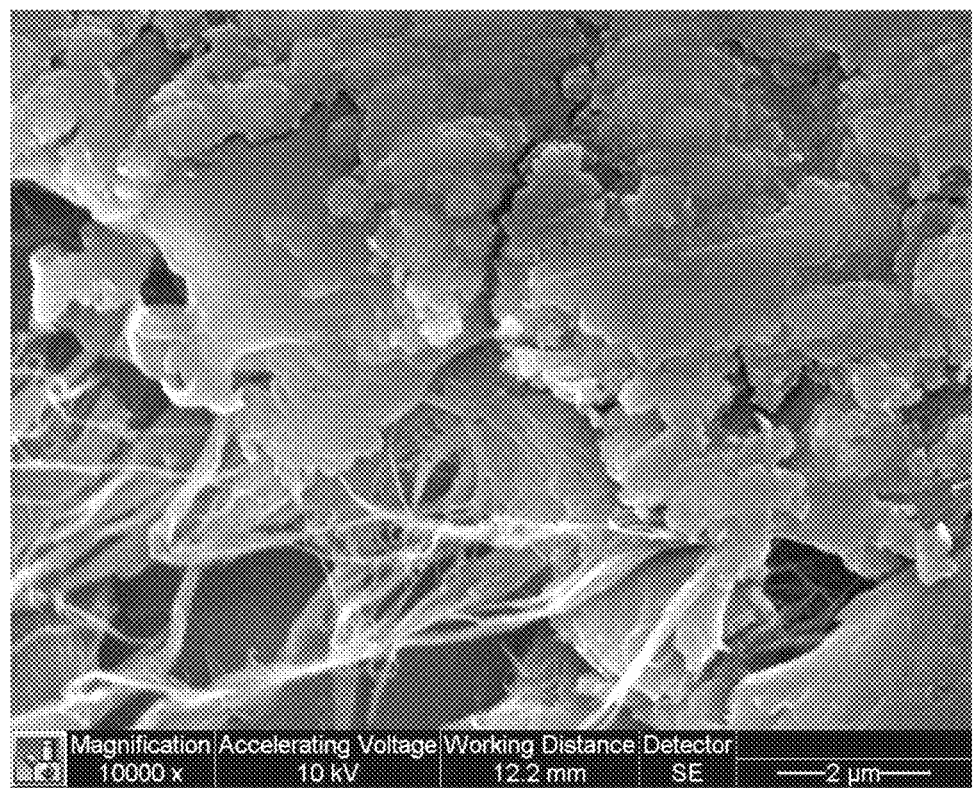
FIG. 7 (see 2 micron bar) shows a portion of Minute Fibril material with entrapped biofilm material, as imaged by SEM after use in cleaning the biofilm from a channel.

TBF was grown in a flow reactor using multispecies organisms (*Enterococcus faecalis* ("EF," ATCC 29212), *Pseudomonas aeruginosa* ("PA," ATCC 27853), *Candida albicans* ("CA," ATCC 14053)), as described elsewhere herein. Six-foot sections of 3.2 mm and 1.6 mm diameter Teflon® tubes bearing the biofilm were tested for cleaning efficiency with Minute Fibril (cellulose) gels made at 2% by weight in water or surfactant solution at flow rates between 20-70 mL/minute. The tubes were sampled before and after cleaning and investigated by SEM and culture methods. Positive and negative controls were used and the results were compared with conventional manual cleaning as described below in "Method." SEM micrographs of sliced open tubing before (FIG. 5A) and after cleaning (FIG. 5B) showed unparalleled/complete biofilm removal from the surface despite the high adhesion strength known for multispecies biofilms. These positive results are supported by culture results of the same tube sections as summarized in the Tables below. Biofilm removal from the 1.6 mm A/W channel was complete in repeated experiments, while manual cleaning could not remove the biofilm at all (FIG. 5C). Also, there was excellent removal of biofilm (more than 6 log reduction) from the 3.2 mm S/B channel, as supported by SEM and culture results. Overall, these very positive results demonstrate that the Minute Fibril cleaning technology has the potential of removing biofilm (matrix and organisms) from endoscopes compared to current methods. The effective removal of biofilm will prevent infections such as CRE. Importantly, the technology is capable of effectively cleaning biofilm from the narrow A/W channels that cannot be brushed with current methods.

TABLE 3.2 mm Channel (Sq. Area 183.851 cm$^2$)

| | | cfu/cm2 | cfu/6-ft | Log$_{10}$cfu/6-ft | RF (log reduction) |
|---|---|---|---|---|---|
| Positive | EF | 1.24 × 10$^6$ | 2.28 × 10$^8$ | 8.357 | |
| Control | PA | 2.64 × 10$^7$ | 4.85 × 10$^9$ | 9.686 | |
| Negative | EF | 0 | 0 | | |
| Control | PA | 0 | 0 | | |
| Test 1 | EF | 0 | 0 | | 8.357 |
| | PA | 0 | 0 | | 9.686 |
| Test 2 | EF | 0.28 × 10 | 5.20 × 10$^2$ | 2.716 | 5.641 |
| | PA | 2.97 × 10 | 5.46 × 10$^3$ | 3.737 | 5.949 |
| Manual | EF | 0 | 0 | | 8.357 |
| Clean | PA | 7.85 × 10$^2$ | 1.44 × 10$^5$ | 5.160 | 4.526 |

TABLE 1.6 mm Channel (Sq. Area 91.925 cm$^2$)

| | | cfu/cm2 | cfu/6-ft | Log$_{10}$cfu/6-ft | RF (log reduction) |
|---|---|---|---|---|---|
| Positive | EF | 4.40 × 10$^6$ | 4.05 × 10$^8$ | 8.607 | |
| Control | PA | 6.55 × 10$^5$ | 6.02 × 10$^7$ | 7.780 | |
| Negative | EF | 0 | 0 | | |
| Control | PA | 0 | 0 | | |
| Test 1 | EF | 0 | 0 | | 8.607 |
| | PA | 0 | 0 | | 7.780 |
| Test 2 | EF | 0 | 0 | | 8.607 |
| | PA | 0 | 0 | | 7.780 |
| Manual | EF | 5.54 × 10$^4$ | 5.09 × 10$^6$ | 6.707 | 1.900 |
| Clean | PA | 4.24 × 10$^4$ | 3.90 × 10$^6$ | 6.591 | 1.189 |

Example 9—Cleaning Bioburden from an Endoscope

Soiling of endoscope was made with the ATS-T with the *Enterococcus faecalis* (EF) (ATCC 29212) bacteria. EF was used because or it high degree of adhesion to channel surface. The endoscope used was Olympus Colonoscope CF-Q160L. The soiling mixture was left in the endoscope for 2 hours. After 2 hrs, cleaning and rinsing was done according to the protocol and as described in the previous examples. Harvesting the organism or organic soil from the channels was done twice in sequence to ensure a near perfect recovery. The cleaning composition as 0.7% Exilva in modified CS-19. For the air/water channel (A/W, ID 1.2 mm) the cleaning flow was 8 mL/min to a total of 250 mL, with 1,000 mL of rinse. For the SB channel (ID 3.7 mm) the cleaning flow was 12 mL/min to a total of 400 mL, with 1,000 mL of rinse.

The results met cleaning specifications for bioburden. For bacteria, there was in one experiment a 4 log$_{10}$ reduction, and in another a near 4 log$_{10}$ reduction.

This example confirms the effectiveness of cleaning according to embodiment of the invention in actual endoscopes. This example also shows that the technology applied to endoscope produces the same results as in the tube experiments described in the previous examples. Both air/water and suction/biopsy channels are cleaned to very high levels without manual brushing or other manipulation. The data also show that removal of organic soil is extremely successful as was the case for testing in Teflon tubes, as detailed in previous examples.

Example 10—Enhanced Biofilm Cleaning

Under the conditions utilized (flow time, etc.), a Minute Fibril composition did not fully remove BBF, but that composition with added microcrystalline cellulose (NT-200 from FMC Corp.) did remove the BBF BBF was formed in 3.7 mm diameter Teflon tube over 8 days according to protocol as described elsewhere herein. The same tube was divided in two sections and was evaluated for BBF removal using two compositions (241 and 242) under similar flow conditions as provided in the Table below. The suspending fluid was substantially similar to Modified CS-19.

| | | Feed Composition | | | |
|---|---|---|---|---|---|
| | I.D. | Main Component | | Additive | |
| Run# | (mm) | Description | Wt. % | Description | Wt. % |
| 241 | 3.7 | 3:1 Epl/Ef | 1.9 | NT200 w fibers | 2.00 |
| 242 | 3.7 | 3:1 Epl/Ef | 1.9 | none | 0.00 |

Using the Anton Parr Rheometer Model 501, frequency sweeps showed that Composition 241 has significantly high elastic properties [high G' (2500 Pa) and low G" (500 Pa)] compared to Composition 241 where G' and G" have low values between [(210 and 260 Pa)]. Amplitude sweeps (plots of G' and G" versus shear stress) of the two compositions show that the cross over shear stress value of Composition 241 is about 45 Pa while that of Composition 242 was only about 13 Pa (FIG. 2). Since the cross over shear stress value is an indication of gel network strength (yield shear stress), Composition 241 is much stronger gel network compared to Composition 242. The results of this Example indicate that network stiffness as demonstrated G' and G" and their relative values as well as network strength as indicated by yield shear stress are important in determining the ability of the network to remove contaminants as exemplified here by BBF.

Not to be bound by theory, the stiffness (G' or elastic modulus) and strength of the gel network (yield shear stress) is usefully larger than that of the biofilm in order to achieve its more complete removal. Literature data indicate that G' of biofilms can range from less than 100 Pa to more than 2000 Pa (Stoodley et al., Structural deformation of bacterial biofilms caused by short-term fluctuations in fluid shear: an in situ investigation of biofilm rheology," Biotechnol Bioeng. 1999 Oct. 5; 65(1): 83-92). In embodiments, the network needs to be strong enough, having high yield shear stress, so that it can maintain sufficient elastic properties during flow in order achieve effective removal of biofilm as exemplified by BBF. Gel network compositions can be made to satisfy such requirements according to embodiments of the invention.

Example 11—Carbopol vs. Minute Fibrils on BBF

BBF was formed in a 1.37 mm Teflon tube over 8 days according to the protocol as described elsewhere herein. Biofilm removal from the tube was evaluated using two compositions: a) carbopol (Ultrez 10-Lubrizol) gel made at 0.17% by weight at pH which was adjusted by triethanol amine TEA) as recommended by Lubrizol, and b) Minute Fibril composition made using 1.9% by weight of 3:1 mixture of Epl and Ef in liquid vehicle substantially similar to CS-19. Both compositions had viscosities>9,000 mPa·s. The carbopol gel exhibited higher yield shear stress values as can judged by the no flow condition even when the vessel was inverted upside down. The operating parameters during cleaning were similar where the pressure drop was about 2.0 psi/linear foot and the volumetric velocity was about 2 ml/minute. Cleaning effectiveness was measured by SEM, optical microscopy and visual examination.

In formulating carbopol gels the user must be aware that they are sensitive salt concentration and ionic strength as well as to pH more 8.0. The structure of the polymer gel network can fall apart and transform into lower viscosity polymer solution. In contrast, the Minute Fibrils gels of the invention can be formulated at a wide range of pH (from about 3.0 to about 12.0), ionic strength and salt concentration and can accommodate surfactant and cleaning additives as in embodiments of the invention.

The results showed that carbopol is an effective cleaning tool, but comes up short in removing BBF. Only about 10% BBF removal was possible with the carbopol gel compared to about 100% removal with the Minute Fibril composition.

Not being bound by theory, polymer gels even if they possess high viscosity and if they have or do not have a yield shear stress cannot produce mechanical forces at the wall sufficient remove BBF. The very thin nanofibrils of the carbopol gel seem to have low stiffness to cause BBF abrasion and erosion during flow. In contrast the fibers and fibrils of the Minute fibril composition appear to have sufficient stiffness and are able to abrade, destroy and remove BBF as per embodiments of the invention.

NUMBERED EMBODIMENTS

The invention can be further described with reference to the following numbered embodiments:

Embodiment A1

A cleaning composition comprising: (A) a carrier fluid; and (B) Minute Fibrils suspended in the carrier fluid, wherein the composition is protein cleaning effective.

Embodiment A2

The cleaning composition of an A Embodiment, wherein the Minute Fibrils are in a protein cleaning effective amount.

Embodiment A3

The cleaning composition of an A Embodiment, wherein the Minute Fibrils are in a BBF cleaning effective amount.

Embodiment A4

The cleaning composition of an A Embodiment, wherein the composition is BBF cleaning effective.

Embodiment A5

A cleaning composition of an A Embodiment, wherein the composition has one or more of the following features: (1) the Minute Fibrils are comprised of a major portion (50% or more by dry weight) of a composition of Minute Fibrils with a first mean hydrodynamic size and another portion of a composition of Minute Fibrils with a mean hydrodynamic size of 50% or less than the first mean hydrodynamic size; (2) solid particles or stiffening polymer effective to increase a storage modulus or yield shear stress of the composition; or (3) the carrier fluid comprises propylene glycol or a glycol ether in amounts effective to increase cleaning of protein, carbohydrate, fat or biofilm; or (4) gel-forming polymers are added in amounts effective to increase the yield shear stress of the composition; or (5) ionic polymer mixed to increase the storage modulus or yield shear stress of the composition.

Embodiment A6

The cleaning composition of an A Embodiment, wherein the solid particles or microcrystalline cellulose are effective to increase cleaning of BBF or protein.

Embodiment A7

The cleaning composition of an A Embodiment, wherein the solid particles or microcrystalline cellulose are harder than a targeted contaminant but less hard than the channel wall.

Embodiment A8

The cleaning composition of an A Embodiment, wherein at least a portion of the solid particles or microcrystalline cellulose are mixed with the Minute Fibrils in such a way that SEM analysis would show a preference for exterior of flocs of the Minute Fibrils.

Embodiment A9

The cleaning composition of an A Embodiment, wherein the carrier fluid comprises a surfactant.

Embodiment A10

The cleaning composition of an A Embodiment, wherein the w/w percentage of surfactant(s) is less than the w/w percentage of Minute Fibrils.

Embodiment A11

The cleaning composition of an A Embodiment, wherein the composition has a yield shear stress of about 1 Pa to about 100 Pa.

Embodiment A12

The cleaning composition of an A Embodiment, wherein the composition has a yield shear stress of about 5 Pa to about 100 Pa.

Embodiment A13_Alpha

The cleaning composition of an A Embodiment, wherein the Minute Fibrils are cellulosic.

Embodiment A13_Beta

The cleaning composition of an A Embodiment, wherein the Minute Fibrils are synthetic.

Embodiment A14

The cleaning composition of an A Embodiment, wherein the Minute Fibrils comprise Type A fibrils of, and Type B fibrils, with SEM images showing Type A fibrils connected to Type B fibrils.

Embodiment A15

The cleaning composition of an A Embodiment, wherein the composition displays shear thinning effective to facilitate emptying a six foot length of 3.2 mm ID channel at a pressure of about 30 p.s.i. or less.

Embodiment A16

The cleaning composition of an A Embodiment, wherein the composition displays a shear thinning when measured at a shear rate 3.33/sec and 20/sec by a viscosity reduction of about 2-fold or more.

Embodiment A17

The cleaning composition of an A Embodiment, wherein the Minute Fibrils are comprised of a major portion (50% or more by dry weight) of a composition of Minute Fibrils with a first mean hydrodynamic size and another portion of a composition of Minute Fibrils with a mean hydrodynamic size of 50% or less than the first mean hydrodynamic size.

Embodiment A18

The cleaning composition of an A Embodiment, wherein solid particles are effective to increase a storage modulus or yield shear stress of the composition

Embodiment A19

The cleaning composition of an A Embodiment, wherein stiffening polymer is effective to increase a storage modulus or yield shear stress of the composition.

Embodiment A20

The cleaning composition of an A Embodiment, wherein the stiffening polymer is microcrystalline cellulose.

Embodiment A21

The cleaning composition of an A Embodiment, wherein the carrier fluid comprises propylene glycol or a glycol ether.

Embodiment A22

The cleaning composition of an A Embodiment, wherein gel-forming polymers are added in amounts effective to increase the yield shear stress of the composition.

Embodiment A23

The cleaning composition of an A Embodiment, wherein ionic polymer is mixed to increase the storage modulus or yield shear stress of the composition.

Embodiment A24

The cleaning composition of an A Embodiment, wherein anionic polymer is mixed to increase the storage modulus or yield shear stress of the composition.

Embodiment A25

The cleaning composition of an A Embodiment, wherein cationic polymer is mixed to increase the storage modulus or yield shear stress of the composition.

Embodiment B1

A kit comprising two or more cleaning compositions of an A Embodiment, one configured for use in a channel with an ID of about 1 to about 2 mm, and one configured for use in a channel with an ID of greater than 2 mm to about 4 mm Embodiment C1

The cleaning composition of an A Embodiment defining a body wash, wherein the body wash comprises antimicrobial agents that consist essentially of one or more essential oils.

Embodiment D1

A method of removing contaminants from a surface comprising:
providing a cleaning composition comprising a carrier fluid comprising, suspended in the carrier fluid, Minute Fibrils, or a gel-forming polymer, or a mixture thereof; and
causing the cleaning composition to pass over surface with a bulk shear stress of about 1 Pa to about 100 Pa,
wherein the composition is protein cleaning effective.

Embodiment D2

The method of a D Embodiment, wherein the carrier fluid further comprises a surfactant.

Embodiment D3

The method of a D Embodiment, wherein the cleaning composition is that of any A Embodiment.

Embodiment D4

The method of a D Embodiment, wherein the method removes biofilm.

Embodiment D5

The method of a D Embodiment, wherein the surface is in a channel of ID 4 mm or less, and wherein said biofilm is found 10 cm or more from an opening for the channel.

Embodiment D6

The method of a D Embodiment, wherein the surface is in a channel of ID 2 mm or less.

Embodiment D7

The cleaning method of a D Embodiment, wherein the Minute Fibrils are in a protein cleaning effective amount.

Embodiment D8

The cleaning method of a D Embodiment, wherein the Minute Fibrils are in a BBF cleaning effective amount.

Embodiment D9

The cleaning method of a D Embodiment, wherein the composition is BBF cleaning effective.

Embodiment D10

The method of a D Embodiment, wherein the surface to be cleaned is a narrow channel in a medical device, a surface of a medical device, teeth, a surface of a precision cylinder, a cylinder-engaging surface of a piston, a food preparation surface, skin (including for a surgical scrub), a surface of a gem, a glass surface (including optical glass), a cutting blade surface, a prosthesis (including in vivo), a wound, a filtration membrane, semiconductor material, a heat exchanger tube, a pipe, a cutting tool, or a moldy portion of a building.

Embodiment E1

A cleaning device comprising: (I) a reservoir containing a cleaning composition comprising a carrier fluid comprising (a) suspended in the carrier fluid, Minute Fibrils, or a gel-forming polymer, or a mixture thereof, wherein the composition is protein cleaning effective; and (II) a pump configured to draw cleaning composition from the reservoir and (a) into a channel to be cleaned of diameter of 10 mm or less and a length of 10 cm or more, or (b) onto a confined space over an open surface to be cleaned, providing a bulk shear stress of 1 Pa or higher.

Embodiment E2

The cleaning device of a D Embodiment, wherein the surface to be cleaned is in a channel.

Embodiment E3

The cleaning device of a D Embodiment, wherein the surface to be cleaned is an open surface.

Embodiment E4

The cleaning device of a D Embodiment, wherein the cleaning composition is that of any A Embodiment.

Embodiment F1

A method of storing a medical device having one or more channels of ID 6 mm or less, the method comprising: (A) filling the channels with a sterile composition comprising a carrier fluid comprising, suspended in the carrier fluid, Minute Fibrils, or a gel-forming polymer, or a mixture thereof; and (B) after a period of storage, rinsing the sterile composition out such that the channel is filled with a sterile fluid suitable for use while operating the medical device.

Embodiment F2

The method of an F Embodiment, wherein the sterile composition comprises an antimicrobial or antibiotic.

Embodiment F3

The method of an F Embodiment, wherein the cleaning composition is that of any A Embodiment.

INCORPORATED APPENDICES

Attached to Provisional B (NOVA003P2) are the following Appendices sharing a common numbering (pages 1-291) that are incorporated herein by reference in their entirety:

TABLE

| | |
|---|---|
| 1 | COMPOSITIONS AND METHODS FOR DECONTAMINATION, CLEANING, DISINFECTION, STORAGE AND STERILIZATION, p. 1 |
| 2 | Various parameters, p. 153 |
| 3 | Elasticity and Stiffness, p. 165 |

| | TABLE-continued |
|---|---|
| 4 | Cleaning of external surfaces, p. 167 |
| 5 | Endoscope Cleaning Apparatus, p. 177 |
| 6 | Advanced Cleaning Endoscope Tubes Using Plug Flow of Microfibrillated Cellulose, p. 204 |
| 7 | Biological testing results, p. 262 |
| 8 | Prep Gel etc., p. 285 |
| 1 | COMPOSITIONS AND METHODS FOR DECONTAMINATION, CLEANING, DISINFECTION, STORAGE AND STERILIZATION, p. 1 |
| 2 | Various parameters, p. 153 |
| 3 | Elasticity and Stiffness, p. 165 |
| 4 | Cleaning of external surfaces, p. 167 |
| 5 | Endoscope Cleaning Apparatus, p. 177 |
| 6 | Advanced Cleaning Endoscope Tubes Using Plug Flow of Microfibrillated Cellulose, p. 204 |
| 7 | Biological testing results, p. 262 |
| 8 | Prep Gel etc., p. 285 |

This invention described herein is of a cleaning composition and methods of forming and using the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. More specifically, those of skill will recognize that any embodiment described herein that those of skill would recognize could advantageously have a subfeature of another embodiment, is described as having that subfeature Publications and references, including but not limited to patents and patent applications, cited in this specification and in the priority filings (with their appendices) are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A method of removing biofilm from a surface, comprising:
providing a cleaning composition comprising a carrier fluid comprising in the carrier fluid polymer comprising Minute Fibrils, the polymer forming an entangled network structure, the Minute Fibrils comprising thicker fibrils, from which branch thinner fibrils, the thicker fibrils having a diameter from about 250 to about 20,000 nm, the thinner fibrils contributing to the entangled network structure, the composition having a yield shear stress of more than 1 Pa, and a storage modulus at 0 rad/s of 200 Pa or higher; and
causing the cleaning composition to pass over the surface driven by a pressure drop effective to render the composition build-up biofilm (BBF) cleaning effective and protein cleaning effective.

2. The method of claim 1, wherein the carrier fluid further comprises a surfactant.

3. The method of claim 1, wherein the surface is in a channel of ID 6 mm or less, and wherein said biofilm is found 10 cm or more from an opening for the channel.

4. The method of claim 3, wherein the surface is in a channel of ID 4 mm or less.

5. The cleaning method of claim 1, wherein the surface to be cleaned is a narrow channel in a medical device, a surface of a medical device, an oral cavity, a tooth, a surface of a precision cylinder, a surgical field, a cylinder-engaging surface of a piston, a food preparation surface, skin, mucosa, a surface of a gem, a glass surface, a cutting blade surface, a prosthesis, a wound, a filtration membrane, semiconductor material, a heat exchanger tube, a pipe, a cutting tool, or a moldy portion of a building.

6. The method of claim 1, wherein the Minute Fibrils comprise a mixture of a major portion of a composition of Minute Fibrils with a first mean hydrodynamic size and another portion of a composition of Minute Fibrils with a mean hydrodynamic size of 50% or less than the first mean hydrodynamic size.

7. The method of claim 1, wherein the cleaning composition comprises stiffening polymer effective to increase the storage modulus or a yield shear stress of the composition.

8. The method of claim 7, wherein the stiffening polymer comprises microcrystalline cellulose.

9. The method of claim 1, wherein the cleaning composition comprises inorganic particles.

10. The method of claim 1, wherein the cleaning composition comprises glycol or glycol ether in an amount effective to increase cleaning of protein, carbohydrate, fat or biofilm.

11. The method of claim 1, wherein the cleaning composition comprises, in the entangled network of polymer, in addition to the Minute Fibril polymer, additional polymer added in amounts effective to increase the yield shear stress of the composition.

12. The method of claim 1, wherein the cleaning composition comprises additional polymer effective to increase a storage modulus or yield shear stress of the composition.

13. The method of claim 1, wherein the cleaning composition has a yield shear stress of more than 5 Pa.

14. The method of claim 1, wherein the Minute Fibrils comprise fibrils of diameter from about 10 to about 90 nm and fibrils of diameter from about 100 to about 20,000 nm.

15. The method of claim 1, wherein the cleaning composition displays a shear thinning when measured at shear rates of 3.33/sec and 20/sec such that a viscosity of the cleaning composition is reduced by 2-fold or more.

16. The method of claim 1, wherein the surface to be cleaned is in a channel of an endoscope.

17. The method of claim 1, wherein the carrier fluid is aqueous.

18. The method of claim 1, wherein the carrier fluid comprises nonaqueous solvent.

19. The method of claim 1, wherein the Minute Fibrils comprise cellulosic Minute Fibrils.

20. A method of removing biofilm from a surface within a channel, said method comprising:
providing a cleaning composition comprising a carrier fluid and polymer comprising Minute Fibrils in said carrier fluid, the polymer forming an entangled network structure, the Minute Fibrils comprising thicker fibrils, from which branch thinner fibrils, the thicker fibrils having a diameter from about 250 to about 20,000 nm, the thinner fibrils contributing to the entangled network structure, the composition having a yield shear stress of more than 1 PA, and a storage modulus at 0 rad/s of 200 Pa or higher; and causing said cleaning composition to move over said surface with a sufficient pressure drop to be protein cleaning effective.

21. The method of claim 20, wherein the cleaning composition comprises surfactant and stiffening polymer effective to increase a storage modulus or yield shear stress of the composition.

22. The method of removing contaminants from the surface in the channel of claim 20,
wherein the method is effective to remove 99.5% or more of protein contaminants on the surface and 99.5% or more of carbohydrate contaminants on the surface.

23. The method of claim 22, wherein the method is effective to achieve a Reduction Factor for reduction of bacteria of about 6.0 or higher.

24. A method of removing biofilm from a surface, said method comprising:
providing a cleaning composition comprising a carrier fluid and polymers comprising Minute Fibrils in said carrier fluid, the polymer forming an entangled network structure, the Minute Fibrils comprising thicker fibrils, from which branch thinner fibrils, the thicker fibrils having a diameter from about 250 to about 20,000 nm, the thinner fibrils contributing to the entangled network structure, the composition having a yield shear stress of more than 1 Pa, a storage modulus at 0 rad/s of 200 Pa or higher, and having a viscosity of 500 mPa-s or higher; and
causing said cleaning composition to move over said surface with a sufficient pressure drop at said surface to render the composition build-up biofilm (BBF) cleaning effective.

25. The method of claim 24, wherein the cleaning composition comprises surfactant and stiffening polymer effective to increase a storage modulus or yield shear stress of the composition.

26. The method of claim 14, wherein the composition comprises fibrils of diameter from about 300 to about 20,000 nm.

27. The method of claim 12, wherein the additional polymer comprises crosslinked polymer.

28. The method of claim 27, wherein the crosslinked polymer comprises crosslinked polyacrylic acid or salts thereof.

29. The method of claim 14, wherein the composition comprises fibrils of diameter from about 250 to about 15,000 nm.

30. The method of claim 1, wherein the viscosity of the cleaning composition is from about 500 to about 10,000 cP.

31. The method of claim 1, wherein the linear velocity of the cleaning composition over the surface is from about 1 cm/sec to about 27 cm/sec.

32. The method of claim 1, wherein the method is effective to reduce adherent protein by 50-fold or more to a level of about 6.4 µg/cm$^2$ or less.

33. The method of claim 1, wherein the Minute Fibrils comprise fibrils from plant cellulose.

34. The method of claim 5, wherein the prosthesis is cleaned while implanted in a patient.

35. The method of claim 2, wherein a w/w concentration of said surfactant is less than a w/w concentration of said Minute Fibrils.

36. The method of claim 20, wherein the the method comprises flowing the cleaning composition through the channel in a plug flow.

37. The method of claim 1, wherein the surface is in an interior of a channel and causing the composition to pass over the surface comprises flowing the composition through the channel.

38. The method of claim 1, wherein at least some of the Minute Fibrils have diameter greater than about 250 nm.

* * * * *